US010369121B2

(12) United States Patent
Cho et al.

(10) Patent No.: US 10,369,121 B2
(45) Date of Patent: Aug. 6, 2019

(54) PHARMACEUTICAL COMPOSITION FOR PREVENTING OR TREATING IMMUNE DISEASES OR INFLAMMATORY DISEASES, CONTAINING BIGUANIDE DERIVATIVE COMPOUND AS ACTIVE INGREDIENT

(71) Applicant: THE CATHOLIC UNIVERSITY OF KOREA INDUSTRY—ACADEMIC COOPERATION FOUNDATION, Seoul (KR)

(72) Inventors: Mi-La Cho, Seoul (KR); Chul-Woo Yang, Seoul (KR); Dong-Yun Shin, Seoul (KR); Min-Jung Park, Incheon (KR); Seon-Yeong Lee, Suwon-si (KR); Sung-Hee Lee, Seoul (KR); Eun-Ji Yang, Seoul (KR); Hye-Jin Son, Seoul (KR); Eun-Kyung Kim, Seoul (KR); Jae-Kyung Kim, Cheonan-si (KR)

(73) Assignee: The Catholic University of Korea Industry-Academic Cooperation Foundation (KR)

( * ) Notice: Subject to any disclaimer, the term of this patent is extended or adjusted under 35 U.S.C. 154(b) by 59 days.

(21) Appl. No.: 15/502,981

(22) PCT Filed: Aug. 25, 2014

(86) PCT No.: PCT/KR2014/007898
§ 371 (c)(1),
(2) Date: Feb. 9, 2017

(87) PCT Pub. No.: WO2015/026215
PCT Pub. Date: Feb. 26, 2015

(65) Prior Publication Data
US 2017/0333370 A1 Nov. 23, 2017

(30) Foreign Application Priority Data

Aug. 23, 2013 (KR) ........................ 10-2013-0100617
Aug. 25, 2014 (KR) ........................ 10-2014-0110919

(51) Int. Cl.
*A61K 31/155* (2006.01)
*C07C 279/18* (2006.01)
*C07C 279/20* (2006.01)
*C07C 279/26* (2006.01)

(52) U.S. Cl.
CPC .......... *A61K 31/155* (2013.01); *C07C 279/18* (2013.01); *C07C 279/26* (2013.01); *A61K 2121/00* (2013.01); *A61K 2300/00* (2013.01)

(58) Field of Classification Search
None
See application file for complete search history.

(56) References Cited

U.S. PATENT DOCUMENTS

| 6,673,908 B1 * | 1/2004 | Stanton, Jr. |
| 2011/0053941 A1 * | 3/2011 | Mautino |
| 2013/0059916 A1 | 3/2013 | Rocchi et al. |

FOREIGN PATENT DOCUMENTS

| KR | 10-2011-0081095 | 7/2011 |
| KR | 10-2013-0015669 | 2/2013 |
| KR | 10-2013-0031229 | 3/2013 |
| KR | 10-2013-0129496 | 11/2013 |

OTHER PUBLICATIONS

Nath et al., "Metformin Attenuated the Autoimmune Disease of the Central Nervous System in Animal Models of Multiple Sclerosis", Journal of Immunology, 2009, vol. 182, pp. 8005-8014.*
Krysiak et al., "Lymphocyte-suppressing and systemic anti-inflammatory effects of high-dose metformin in simvastatin-treated patients with impaired fasting glucose", Atherosclerosis, vol. 225, pp. 403-407, available online Oct. 12, 2012.*

* cited by examiner

*Primary Examiner* — Savitha M Rao
*Assistant Examiner* — Gregg Polansky
(74) *Attorney, Agent, or Firm* — JHK Law; Joseph Hyosuk Kim

(57) ABSTRACT

The present invention relates to a biguanide derivative compound capable of effectively preventing and treating immune diseases. The biguanide-based derivative compound according to the present invention inhibits the generation of IL-17 and TNF-α, which are inflammatory cytokines, increases the activity of regulatory T cells having an immunomodulatory function, and exhibits excellent therapeutic effects in animal models of immune diseases. Accordingly, the biguanide-based derivative compound can be usefully used as an immunosuppressant or a pharmaceutical composition capable of preventing or treating various immune diseases, such as autoimmune diseases, inflammatory diseases, and transplant rejection, caused by the dysregulation of immune responses.

6 Claims, 16 Drawing Sheets

Regulation of cytotoxicity effect

Regulation of autoantibody generation immune response

Regulation of generation of inflammatory cytokines

Regulation of cytotoxicity effect

Regulation of generation of inflammatory cytokines

Regulation of cytotoxicity effect

Regulation of autoantibody generation immune response

Regulation of generation of inflammatory cytokines

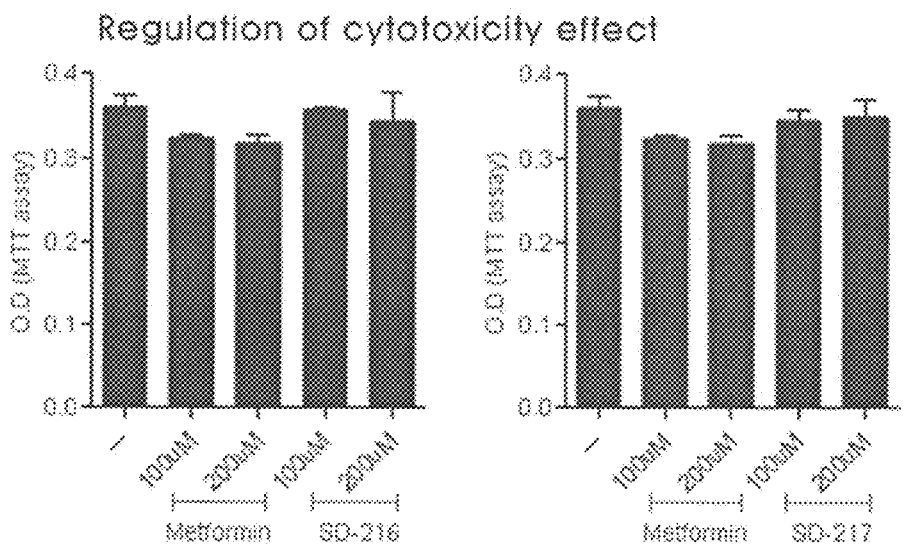
FIG 16A Regulation of cytotoxicity effect
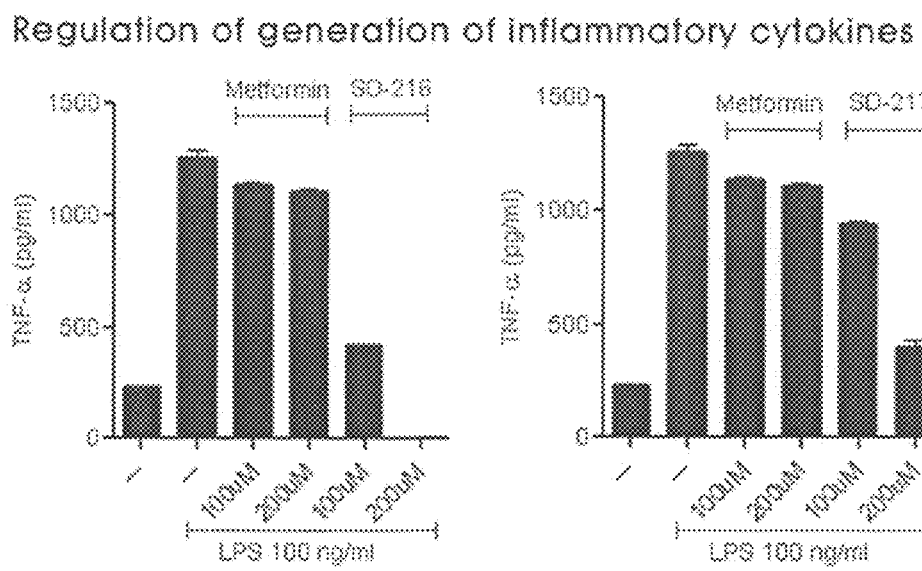
FIG 16B Regulation of generation of inflammatory cytokines

PHARMACEUTICAL COMPOSITION FOR PREVENTING OR TREATING IMMUNE DISEASES OR INFLAMMATORY DISEASES, CONTAINING BIGUANIDE DERIVATIVE COMPOUND AS ACTIVE INGREDIENT

TECHNICAL FIELD

The present invention relates to a biguanide derivative compound capable of effectively preventing and treating immune diseases or inflammatory diseases.

BACKGROUND ART

Immune diseases mean diseases in which the components of an immune system cause, mediate, or contribute pathological conditions, and particularly, inflammatory disorder is one of the most important health problems around the world. Inflammation generally means a localized protective response of body tissues against the host intrusion by foreign substances or harmful stimuli. The cause of inflammation includes infectious causes such as bacteria, viruses, and parasites; physical causes such as burns or radiation; chemicals such as toxins, drugs, or industrial agents; immune responses such as allergy and autoimmune responses, conditions associated with oxidative stress, or the like.

The inflammation is characterized by symptoms such as pain, a red phenomenon, swelling, heat, and an eventual functional loss of an infected area. These symptoms are results of a series of complex interactions occurred between cells in the immune system. Due to the cell reaction, as a result, an interaction network of various groups of inflammatory mediators [proteins (for example, cytokines, enzymes (e.g., protease, peroxidase), major basic proteins, adhesive molecules (ICAM, VCAM), lipid mediators (e.g., eicosanoid, prostaglandin, leukotriene, platelet activating factors (PAF)), reactive oxygen species (e.g., hydroperoxide, superoxide anion $O^{2-}$, nitric oxide (NO), etc)] is generated. However, most of the mediators are also normal cell activity regulators. Accordingly, while the host is not controlled due to the lack of the inflammatory response, the host is damaged (that is, infected), and therefore, due to the chronic inflammation, partially, some of the aforementioned mediators are excessively generated and thus, the mediated inflammatory diseases are caused.

Further, an autoimmune disease which is one of the immune diseases has a feature that the immune system causes a spontaneous response by attacking its organ. The responses are caused by recognition of auto-antigen by the T lymphocytes and thus humoral (generation of auto-antigens) and cellular (an increase in cytotoxicity activity of lymphocytes and macrophages) immune responses are caused. The autoimmune diseases include rheumatic diseases, psoriasis, systemic dermatomyositis, multiple sclerosis, lupus erythematosus, deterioration of immune responses by antigens, i.e., asthma, drug or food allergies, or the like. The diseases are limitative and chronic diseases, and in some cases become fatal. The effective treating method capable of treating the diseases until now is not present. Therefore, drugs, medicines, or media capable of reducing or alleviating the diseases in the progress of the disease may become an important solution means for a patient's health.

Concentrated efforts to find appropriate drugs and methods by searching methods for treating the autoimmune diseases have been made. Today, the treatment of autoimmune diseases is mainly based on the use of immunosuppressive drugs, for example, glucocorticoids, calcineurin inhibitors, and antiproliferative-anti metabolites. However, these drugs act on a variety of targets, thereby entirely decreasing the immune function. Further, in the case of using the pharmacotherapies for a long time, various cytotoxic effects may be shown and the immune system is non-specifically suppressed to cause infection or cancers of patients. Calcineurin and glucocorticoid have another problem due to their nephrotoxicity and diabetes induced characteristics, and thus in the case of some of clinical symptoms (e.g., renal insufficiency, diabetes, etc.), the use thereof is restricted.

Accordingly, as a substance capable of treating immune diseases such as autoimmune diseases and inflammatory diseases, development of novel immune diseases therapeutic agents having an excellent treating effect without side effects is required.

As a result, the inventors synthesized various kinds of biguanide derivative compounds and verified these activities while finding materials with fewer human side effects capable of effectively preventing or treating immune diseases or inflammatory diseases and thus verified effects of inhibiting generation of IL-17 and TNF-α as inflammatory cytokines, increasing activity of regulatory T cells having an immunomodulatory function, and having a therapeutic effect in vivo in the case of applying the biguanide derivative compound of the present invention to an inflammatory bowel disease animal model and an acute graft versus host disease animal model, and completed the present invention.

DISCLOSURE

Technical Problem

One aspect of the present invention provides a pharmaceutical composition for preventing or treating immune diseases or inflammatory diseases, in which the pharmaceutical composition includes a biguanide derivative compound or a pharmaceutically acceptable salt thereof as an active ingredient.

In an embodiment of the present invention, the biguanide derivative compound may be at least one compound selected from the group consisting of 1-(3,5-dimethoxyphenyl)biguanide, 1-(4-(pentyloxy)biguanide, 1-(4-isopropylphenyl) biguanide, 1-(2-fluorophenyl)biguanide, 1-(3-isopropylphenyl)biguanide, 1-(4-isopropoxyphenyl)biguanide, 1-(3,5-dimethoxyphenyl)biguanide, 1-(2-chlorophenyl)biguanide, 1-(4-fluorophenyl)biguanide, 1-(3-trifluoromethylphenyl) biguanide, 1-(3-fluorophenyl)biguanide, 1-(2,4-difluorophenyl)biguanide, 1-(2,3,4-trifluorophenyl)biguanide, 1-(2,5-difluorophenyl)biguanide, 1-phenethyl biguanide, 1-cyclohexyl biguanide, 1-allyl biguanide, 1-benzyl biguanide, 1-(3,4-difluorobenzyl)biguanide, 1,1-dipropyl biguanide, 1-isopropyl biguanide, and 1,1-diethyl biguanide.

In an embodiment of the present invention, the biguanide derivative compound may have a therapeutic effect through a mechanism of reducing or suppressing generation of inflammatory cytokine.

In an embodiment of the present invention, the inflammatory cytokine may be IL-17 or TNF-α.

In an embodiment of the present invention, the biguanide derivative compound may have a therapeutic effect through a mechanism of promoting or increasing activity of regulatory T cells.

In an embodiment of the present invention, the biguanide derivative compound may be included in the concentration of 1 μM to 1,000 μM in the composition.

In an embodiment of the present invention, the immune disease may be selected from the group consisting of autoimmune diseases; inflammatory diseases; and transplantation rejection diseases of cells, tissues or organs.

In an embodiment of the present invention, the immune disease may be an inflammatory bowel disease (IBD).

In an embodiment of the present invention, the transplantation rejection disease may be a graft versus host disease.

In an embodiment of the present invention, the immune disease may be selected from the group consisting of Behcet's disease, multiple myositis, skin myositis, autoimmune hematocytopenia, autoimmune myocarditis, atopic dermatitis, asthma, primary cirrhosis, dermatomyositis, Goodpasture syndrome, autoimmune meningitis, Sjogren's syndrome, systemic lupus erythematosus, Addison's disease, alopecia areata, ankylosing myelitis, autoimmune hepatitis, autoimmune mumps, Crohn's disease, insulin-dependent diabetes, dystrophic epidermolysis bullosa, epididymitis, glomerulonephritis, Graves' disease, Guillain-Barre syndrome, Hashimoto's disease, hemolytic anemia, multiple sclerosis, myasthenia gravis, pemphigus vulgaris, psoriasis, rheumatic fever, rheumatoid arthritis, sarcoidosis, scleroderma, spinal arthrosis, thyroiditis, vasculitis, vitiligo, myxedema, pernicious anemia, ulcerative colitis, graft versus host diseases, and obesity.

In an embodiment of the present invention, the inflammatory disease may be selected from the group consisting of gastritis, enteritis, nephritis, hepatitis, chronic obstructive pulmonary diseases (COPD), pulmonary fibrosis, irritable bowel syndrome, inflammatory pain, migraine, headache, back pain, fibromyalgia, fascia disease, viral infection, bacterial infection, fungal infection, burns, injuries by surgical or dental surgery, PGE hyperaemia, atherosclerosis, gout, Hodgkin's disease, pancreatitis, conjunctivitis, iritis, scleritis, uveitis, and eczema.

In an embodiment of the present invention, the composition may be administrated to a subject requiring the composition as an object in the amount of 1 to 100 mg (based on a preclinical mouse animal model) per 1 kg as a weight.

Advantageous Effects

The biguanide-based derivative compound according to the present invention inhibits the generation of IL-17 and TNF-α, which are inflammatory cytokines, increases the activity of regulatory T cells having an immunomodulatory function, and exhibits excellent therapeutic effects in animal models of immune diseases. Accordingly, the biguanide-based derivative compound can be usefully used as an immunosuppressant or a pharmaceutical composition capable of preventing or treating the immune diseases or inflammatory diseases, such as autoimmune diseases, inflammatory immune diseases, and transplant rejection diseases, caused by the dysregulation of various immune responses.

DESCRIPTION OF DRAWINGS

FIG. 16 is a result of measuring cytotoxicity (MTT assay) (A) and a change in expression of TNF-α inflammatory cytokine (B) of the biguanide derivative compound of the present invention in normal cells.

MODES OF THE INVENTION

Figure 1A:
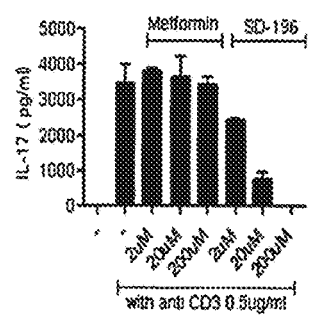
FIG. 1 is a result of analyzing an IL-17 generation amount in cells according to a concentration (2, 20, 200 μM) treatment of a biguanide derivative compound of the present invention in spleen cells isolated from mice by a sandwich ELISA method (A: SD-196, B: SD-216, C: SD-217).

The present invention first finds that the biguanide derivative compound has an effect capable of preventing or treating immune diseases through an immune regulation function and thus, provides a composition for preventing or treating immune diseases containing a biguanide derivative compound or pharmaceutically acceptable salt thereof as an active ingredient.

The biguanide derivative compound of the present invention may be selected from the group consisting of 1-(3,5-dimethoxyphenyl)biguanide, 1-(4-(pentyloxy)biguanide, 1-(4-isopropylphenyl)biguanide, 1-(2-fluorophenyl)biguanide, 1-(3-isopropylphenyl)biguanide, 1-(4-isopropoxyphenyl)biguanide, 1-(3,5-dimethoxyphenyl)biguanide, 1-(2-chlorophenyl)biguanide, 1-(4-fluorophenyl)biguanide, 1-(3-trifluoromethylphenyl)biguanide, 1-(3-fluorophenyl)biguanide, 1-(2,4-difluorophenyl)biguanide, 1-(2,3,4-trifluorophenyl)biguanide, 1-(2,5-difluorophenyl)biguanide, 1-phenethyl biguanide, 1-cyclohexyl biguanide, 1-allyl biguanide, 1-benzyl biguanide, 1-(3,4-difluorobenzyl)biguanide, 1,1-dipropyl biguanide, 1-isopropyl biguanide, and 1,1-diethyl biguanide.

Chemical Formulas of the compound of the present invention are particularly illustrated in Table 1 below.

TABLE 1

Chemical Formulas of biguanide derivative compound of the present invention

| Derivate No. | Chemical Formula |
|---|---|
| 1 | 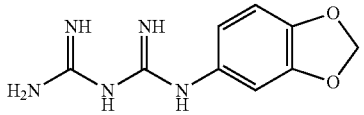 [SMILES: N=C(N)NC(=N)Nc1ccc2c(c1)OCO2] |
| 2 | 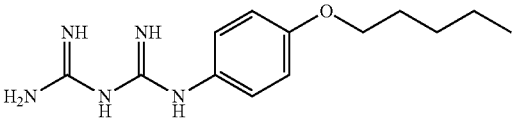 [SMILES: CCCCCOc1ccc(NC(=N)NC(=N)N)cc1] |
| 3 | 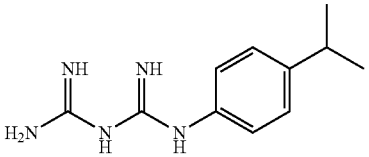 [SMILES: CC(C)c1ccc(NC(=N)NC(=N)N)cc1] |
| 4 | 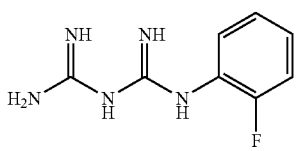 |
| 5 | 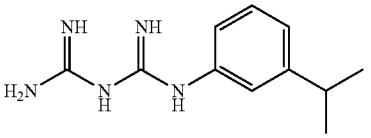 |
| 6 | 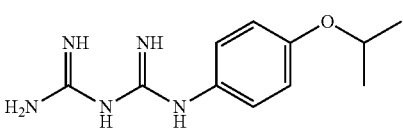 |
| 7 | 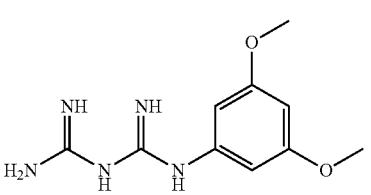 [SMILES: COc1cc(NC(=N)NC(=N)N)cc(OC)c1] |
| 8 | 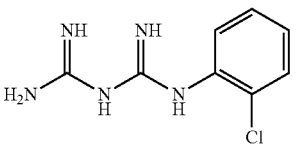 [SMILES: N=C(N)NC(=N)Nc1ccccc1Cl] |
| 9 | 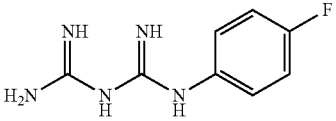 |
| 10 | 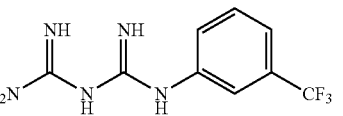 |
| 11 | 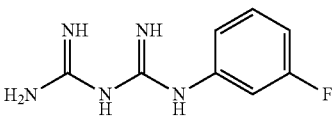 [SMILES: N=C(N)NC(=N)Nc1cccc(F)c1] |
| 12 | 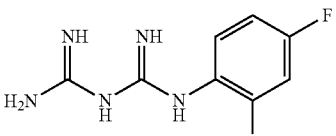 |
| 13 | 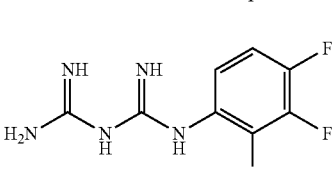 |

TABLE 1-continued

Chemical Formulas of biguanide derivative compound of the present invention

| Derivate No. | Chemical Formula |
|---|---|
| 14 | $H_2N-C(NH)-NH-C(NH)-NH-$ (2,5-difluorophenyl) |
| 15 | $H_2N-C(NH)-NH-C(NH)-NH-CH_2CH_2-$ phenyl |
| 16 | $H_2N-C(NH)-NH-C(NH)-NH-$ cyclohexyl |
| 17 | $H_2N-C(NH)-NH-C(NH)-NH-CH_2-CH=CH_2$ |
| 18 | $H_2N-C(NH)-NH-C(NH)-NH-CH_2-$ phenyl |
| 19 | $H_2N-C(NH)-NH-C(NH)-NH-CH_2-$ (3,4-difluorophenyl) |
| 20 | $H_2N-C(NH)-NH-C(NH)-N(propyl)_2$ |
| 21 | $H_2N-C(NH)-NH-C(NH)-NH-CH(CH_3)_2$ |
| 22 | $H_2N-C(NH)-NH-C(NH)-N(ethyl)_2$ |

The inventors pay attention to the biguanide derivative compound in order to develop a novel immunomodulator for treating immune diseases and verify that the biguanide derivative compound of the present invention can effectively regulate the immune through the following experiment.

In the following Example 2 of the present invention, in order to examine an effect of the biguanide derivative compound on generation of IL-17 as an inflammatory cytokine, the expression degree of IL-17 is measured by an ELISA assay and as a result, in the case of treating the biguanide derivative compound of the present invention, it can be verified that an IL-17 generation amount is significantly reduced (see FIG. 1).

Further, in the following Example 3 of the present invention, in order to examine an effect of the biguanide derivative compound on generation of TNF-α as an inflammatory cytokine, the expression degree of TNF-α is measured by an ELISA assay and as a result, in the case of treating the biguanide derivative compound of the present invention, it can be verified that a TNF-α generation amount is very significantly reduced (see FIG. 2).

Meanwhile, it is known that IL-17 and TNF-α as inflammatory cytokines are greatly increased in inflammatory bowel diseases (IBDs).

The IBD is a chronic and recurrent disease of which the cause is not known and more than 1 million of Americans and millions of people worldwide have the IBD. The IBD is a general cause of the chronic diseases in a large part of the patient population. The IBD is shown by two different types of ulcerative colitis and a Crohns disease. The two types are very clinically similar to each other, but the ulcerative colitis mainly involves inflammation of the colon and the rectum which are opposite to the upper gastrointestinal tract. Meanwhile, the Crohns disease has an effect on a larger part of the digestive tract of the upper internal organ to be more likely to cause malabsorption and chronic vitamin and nutritional deficiencies. People with the IBD suffer symptoms having features such as chronic intestinal inflammation, diarrhea, bleeding, abdominal pain, fever, joint pain, and weight loss. The symptoms are various from light things to heavy things. The IBD may be developed first gradually from the minor discomfort and unknowingly and may be suddenly acute.

Accordingly, in Examples 2 and 3, the inventors verified the reductions in generation amount/expression amount of inflammatory bowel disease-related cytokines IL-17 and TNF-α in vitro according to the treatment of the biguanide derivative compound of the present invention and actually, examined whether the biguanide derivative compound of the present invention had an effect of treating the inflammatory bowel disease.

In the following Example 4 of the present invention, an inflammatory bowel disease animal model was prepared using dextran sodiumsulfate (DSS) and the biguanide derivative compound was applied (administered) herein, and as a result, it was verified that the weight in the inflammatory bowel disease animal model was significantly improved (see FIG. 3). In addition, the biguanide derivative compound of the present invention was applied (administrated) to the inflammatory bowel disease animal model, and as a result, it can be verified that while the cellular inflammatory degree in the colon tissue of the mouse is reduced, the damage in the colon tissue is low and the penetration of the cells is low (see FIG. 4).

Further, based on the above result, a similar experiment was performed even in rheumatoid arthritis and lupus animal models as other immune diseases, and as a result, it was verified that the biguanide derivative compound of the present invention significantly reduced the expression of IL-17 and TNF-α as the inflammatory cytokines and had an inhibitory effect on autoantibody (IgG) generation and the like (see FIGS. 9 to 15).

Through the above results, it was proved that the biguanide derivative compound of the present invention can treat immune diseases through mechanisms such as effectively reducing the generation amount/expression amount of the inflammatory cytokines of IL-17 and TNF-α.

Further, in the following Example 5 of the present invention, an alloresponse inhibition effect of the biguanide derivative compound was examined, and as a result, it can be verified that in the case of treating the biguanide derivative compound of the present invention, the alloresponse is significantly inhibited (see FIG. 6).

Further, in the following Example 6 of the present invention, an effect on the activity of regulatory T cells (hereinafter, briefly abbreviated as 'Treg') of the biguanide derivative compound was examined, and as a result, it can be verified that in the case of treating the biguanide derivative compound of the present invention, the activity of the Treg cell is significantly increased (see FIG. 7).

Further, in the following Example 7 of the present invention, an acute graft versus host disease was prepared and whether an effect of improving or treating the disease by applying (administrating) the biguanide derivative compound thereto was actually present was examined, and as a result, it can be verified that in the case of treating the biguanide derivative compound of the present invention, the survivals of mice with the induced acute graft versus host disease are significantly increased (see FIG. 8).

Through the above results, it was proved that the biguanide derivative compound of the present invention had an excellent effect of regulating the immune through a mechanism of suppressing the alloresponse and increasing the activity of the Treg cell to treat a graft versus host disease as a kind of immune diseases.

Further, as a result of texting an effect of inhibiting cytotoxicity and inflammatory cytokines of the biguanide derivative compound of the present invention by targeting the human cells, like the results, it is verified that the cytotoxicity is not shown and the inflammatory cytokines are efficiently reduced (see FIG. 16).

Therefore, the present invention may provide a composition for preventing or treating immune diseases, in which the composition includes the biguanide derivative compound or the pharmaceutically acceptable salt thereof as an active ingredient.

The biguanide derivative compound of the present invention may be at least one compound selected from the compounds represented by Chemical Formulas 1 to 22 listed in Table 1.

Further, the compound represented by Chemical Formula according to the present invention may be used in a form of a salt, preferably, a pharmaceutically acceptable salt. The salt is preferably an acid addition salt formed by pharmaceutically acceptable free acid, and as the free acid, organic acid and inorganic acid may be used. The organic acid is not limited thereto, but includes citric acid, acetic acid, lactic acid, tartaric acid, maleic acid, fumaric acid, formic acid, propionic acid, oxalic acid, trifluoroacetic acid, benzoic acid, gluconic acid, metasulfonic acid, glycolic acid, succinic acid, 4-toluenesulfonic acid, glutamic acid, and aspartic acid. Further, the inorganic acid is not limited thereto, but includes hydrochloric acid, bromic acid, sulfuric acid, and phosphoric acid.

The compound according to the present invention may be a compound isolated from the natural or prepared by a chemical synthesis method known in the art.

In the present invention, the "immune diseases" mean diseases in which the components of a mammalian immune system cause, mediate, or contribute the pathological conditions of the mammals. Further, the immune diseases may include all diseases in which simulation or stop of the immune response has a compensating effect on the progression of the diseases, and in the present invention, the immune diseases may include diseases caused by hypersensitive immune responses. Examples of the immune diseases are not limited thereto, but may include all of autoimmune diseases; inflammatory diseases; transplantation rejection diseases of cells, tissues or organs, and the like.

Further, in all normal subjects, one of the most important features has ability capable of recognizing, responding, and removing non-self-antigens without harmfully responding to self-antigen substances constituting themselves. As such, the non-response of the living body to the self-antigen is called immunologic unresponsiveness or tolerance.

However, when a problem in inducing or continuously maintaining the self-tolerance occurs, the immune response to the self-antigen occurs and thus a phenomenon in which the self-antigen attacks its tissue occurs, and diseases caused by such a process are called "autoimmune diseases".

Further, the "inflammatory diseases" mean diseases caused by inflammatory substances (inflammatory cytokines) such as tumor necrosis factor-α☐ (TNF-α), interleukin-1 (IL-1), IL-6, prostagladin, luecotriene, or nitric oxide (NO) which is secreted from immune cells such as macrophagocyte by excessively accelerating the human immune system by injurious stimuli such as inflammatory agents or UV irradiation.

Meanwhile, for successful organ transplantation, a recipient's immune rejection response to cells and organs to be transplanted needs to be overcome. A major medium of the transplantation immune rejection response is T cells and a major histocompatibility complex (MHC) which is expressed in a graft is recognized by a T cell receptor and thus the immune response is induced and the transplantation rejection response occurs. The MHC is determined according to a type of glycoprotein antigen, and an immune response which occurs when a histocompatibility antigen is not matched is an obstacle to block the successful transplantation and thus investigation of the accuracy of a histocompatibility antigen test and the matching of the histocompatibility antigen is a very important element.

The human includes many types of histocompatibility antigens, and includes Class I antigens including HLA-A, -B, and -C and Class II antigens including HLA-DR, -DP, and -DQ. A biological function of these antigens is to deliver the antigens to T lymphocytes, and the Class I antigens are expressed in most of nucleated cells and the antigens delivered therethrough are recognized by CD8+ cytotoxic T lymphocytes. The Class II antigens are expressed in dendritic cells known as antigen-presenting cells, B lymphocytes, activated T lymphocytes, macrophages, and the like and have a function to deliver the antigen to CD4+ T lymphocytes. The T lymphocytes recognize the antigens by binding the antigens delivered to the T lymphocytes to the T lymphocyte receptor and recognize the histocompatibility antigens derived from another person other than one's own antigens with a high frequency in the transplantation process. About 1 to 10% of the entire T lymphocytes of a donor or a patient recognize the histocompatibility antigens derived from the patient or the donor to be proliferated by the response thereto and cause a series of immune responses, and the immune response is called an "alloresponse". Further, the T lymphocytes of the donor cause the immune response to the histocompatibility antigen of the patient and it is called a "graft-versus-host disease (GVDH)", and on the contrary, a response to the histocompatibility antigen of the donor caused by the T lymphocytes of the patient is called a "graft rejection response".

Accordingly, in order to reduce an abnormal response by the immune response generated in the grafting process, immunosuppressive agents have been used, and the common object of the immunosuppressive agents is to suppress a T cell-mediated immune response to the graft. Recently, a method for treating graft rejection diseases by suppressing the immune response using the regulatory T cells has been attempted.

Further, in the present invention, the types of immune diseases are not limited thereto, but may include Behcet's disease, multiple myositis, skin myositis, autoimmune hematocytopenia, autoimmune myocarditis, atopic dermatitis, asthma, primary cirrhosis, dermatomyositis, Goodpasture syndrome, autoimmune meningitis, Sjogren's syndrome, systemic lupus erythematosus, Addison's disease, alopecia areata, ankylosing myelitis, autoimmune hepatitis, autoimmune mumps, Crohn's disease, insulin-dependent diabetes, dystrophic epidermolysis bullosa, epididymitis, glomerulonephritis, Graves' disease, Guillain-Barre syndrome, Hashimoto's disease, hemolytic anemia, multiple sclerosis, myasthenia gravis, pemphigus vulgaris, psoriasis, rheumatic fever, rheumatoid arthritis, sarcoidosis, scleroderma, spinal arthrosis, thyroiditis, vasculitis, vitiligo, myxedema, pernicious anemia, ulcerative colitis, graft versus host diseases, obesity and the like.

Further, in the present invention, the inflammatory diseases may include gastritis, enteritis, nephritis, hepatitis, chronic obstructive pulmonary diseases (COPD), pulmonary fibrosis, irritable bowel syndrome, inflammatory pain, migraine, headache, back pain, fibromyalgia, fascia disease, viral infection, bacterial infection, fungal infection, burns, injuries by surgical or dental surgery, PGE hyperaemia, atherosclerosis, gout, Hodgkin's disease, pancreatitis, conjunctivitis, iritis, scleritis, uveitis, eczema, and the like.

Therefore, the composition according to the present invention may be used as a pharmaceutical composition capable of preventing or treating the immune diseases or the inflammatory diseases.

Unless otherwise notified, the term 'treatment' means that a disease, a disorder, or one or more symptoms of the disease or the disorder to which the term is applied is reversed or alleviated, or the progress thereof is inhibited or prevented, and the term 'treating' used in the present invention means a treating action defined as described above. Accordingly, the "treatment" or the "therapy" of the immune diseases in mammals may include one or more treatments below of:

(1) inhibiting a growth of the immune diseases, that is, preventing the development thereof, (2) preventing the spread of the immune diseases, that is, preventing the metastasis thereof, (3) alleviating the immune diseases, (4) preventing the recurrence of the immune diseases, and (5) palliating the symptoms of the immune diseases.

The composition for preventing or treating the immune diseases according to the present invention may include at least one compound among the compounds represented by Chemical Formulas 1 to 22 (see Table 1) or a salt thereof alone in a pharmaceutically effective amount, or at least one pharmaceutically acceptable carrier, excipient, or diluent.

The pharmaceutically effective amount means an amount sufficient to prevent, improve, and treat the symptoms of the immune diseases or the inflammatory diseases.

The pharmaceutically effective amount of the biguanide derivative compound or the salt thereof according to the present invention may be properly changed according to the degree of the symptoms of the immune diseases, an age, a weight, a health state, a sex, an administration route, and a treatment period of a patient, and the like.

Further, the above "pharmaceutically acceptable" generally means a composition which does not generally cause an allergic reaction such as gastroenteric trouble and dizziness or a similar reaction thereto, when the amount is physiologically acceptable and administrated to the human body. Examples of the carrier, the excipient, and the diluent may include lactose, dextrose, sucrose, sorbitol, mannitol, xylitol, erythritol, maltitol, starch, acacia rubber, alginate, gelatin, calcium phosphate, calcium silicate, cellulose, methyl cellulose, polyvinylpyrrolidone, water, methyl hydroxybenzoate, propyl hydroxybenzoate, talc, magnesium stearate, and mineral oil. Further, filler, an anti-coagulant, a lubricant, a wetting agent, a flavoring, an emulsifier, a preservative, and the like may be additionally included.

Further, the composition of the present invention may be formulated by using a method known in the art so as to provide rapid, sustained, or delayed release of an active component after being administered to the mammal. The formulation may be a form of a powder, a granule, a tablet, an emulsion, syrup, an aerosol, a soft or hard gelatin capsule, a sterile injection solution, and a sterile powder.

Further, the composition for preventing or treating the immune diseases according to the present invention may be administrated through various routes including oral, percutaneous, subcutaneous, intravenous and intramuscular tissues, and the administration amount of the active component may be properly selected according to various factors such as an administration route, an age, a sex, and a weight of a patient, and the severity of the patient. The composition for preventing or treating the immune diseases according to the present invention may be administrated by combining a known compound having an effect of preventing, improving, or treating the symptoms of the immune diseases.

Further, the present invention provides a use of a composition containing the biguanide derivative compound for preparing a drug for preventing or treating immune diseases or inflammatory diseases as an active ingredient. The composition of the present invention containing the biguanide derivative compound as an active ingredient may be used for preparing a drug for preventing or treating the immune diseases or the inflammatory diseases.

The present invention also provides a method for preventing or treating immune diseases or inflammatory diseases, in which the method includes administrating a pharmaceutical composition of the present invention to a mammal in a therapeutically effective amount.

The term "mammal" used herein means a mammal which is a target for treatment, observation, or testing, and preferably, the human.

The term "therapeutically effective amount" used herein means an amount of an active ingredient or a pharmaceutical composition which induces a biological or medical response in a tissue system, an animal, or the human which is considered by researchers, veterinarian, physician, or other clinicians, and includes an amount of inducing alleviation of symptoms of diseases or disorders to be treated. It is apparent to those skilled in the art that an effective dose and the number of administration times on the treatment for the active ingredient of the present invention are changed according to a desired effect. Therefore, an optimal dose to be administrated may be easily determined by those skilled in the art, and may be adjusted according to various factors including a type of disease, severity of the disease, the contents of an active ingredient and other ingredients contained in the composition, a type of formulation, and an age, a weight, a general health status, a sex, a diet, an administration time, a route of administration, a secretion ratio of the composition, a treating period, and simultaneously used drugs.

Hereinafter, the present invention will be described in more detail through Examples. Examples are to describe the present invention in detail and the scope of the present invention is not limited to Examples.

Example 1

Synthesis and Preparation of Biguanide Derivative Compound According to the Present Invention Biguanide derivatives 1 to 22 represented by Chemical Formulas in Table 1 below were prepared by the following method.

1. Synthesis of SD-000170, SD-000179, SD-000180, and SD-000181: Aniline was dissolved in acetonitrile and then added with 1 M of hydrochloric acid by 1 equivalent. In addition, dicyandiamide was added, a reactant was heated up to 100° C., and then a crystalline material was filtered.

2. Synthesis of SD-000171, SD-000172, SD-000173, SD-000174, SD-000175, SD-000177, and SD-000178: Aniline was dissolved in acetonitrile and then added with 1 M of hydrochloric acid by 1 equivalent. In addition, dicyandiamide was added, a reactant was heated up to 100° C., and then purified by a column chromatography.

3. Synthesis of SD-000216, SD-000217, SD-000218, and SD-000219: Aniline was dissolved in acetonitrile and then added strong hydrochloric acid by 1 equivalent. In addition, dicyandiamide was added, a reactant was heated up to 175° C., and then a crystalline material was filtered.

4. Synthesis of SD-000176 and SD-000196: Aniline was dissolved in acetonitrile and then added strong hydrochloric acid by 1 equivalent. Dicyandiamide was added, a reactant was heated up to 170° C., and then a crystalline material was filtered.

5. Synthesis of SD-000183, SD-000184, and SD-000198: Aniline was dissolved in acetonitrile and then added strong hydrochloric acid by 1 equivalent. In addition, dicyandiamide was added, a reactant was heated up to 150° C., and then a remaining crystalline material was filtered.

6. Synthesis of SD-000195: Aniline (amine) was dissolved in acetonitrile and then added strong hydrochloric acid by 1 equivalent. In addition, dicyandiamide was added, a reactant was heated up to 140° C., and then a crystalline material was filtered.

TABLE 2

22 types of biguanide derivative compounds of the present invention

| No | Compound code | Compound structure | Compound name |
|---|---|---|---|
| 1 | SD-000170 | 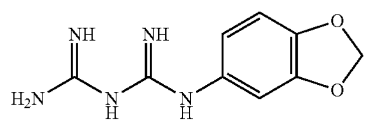 [SMILES: N=C(N)NC(=N)Nc1ccc2c(c1)OCO2] | 1-(3,4-methylenedioxyphenyl)biguanide |
| 2 | SD-000171 | 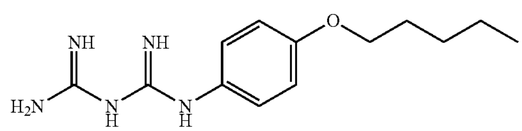 [SMILES: CCCCCOc1ccc(NC(=N)NC(=N)N)cc1] | 1-(4-(pentyloxy)phenyl)biguanide |
| 3 | SD-000172 | 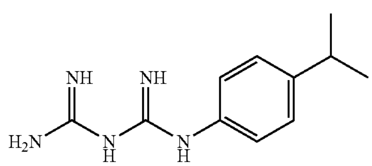 [SMILES: CC(C)c1ccc(NC(=N)NC(=N)N)cc1] | 1-(4-isopropylphenyl)biguanide |
| 4 | SD-000173 | 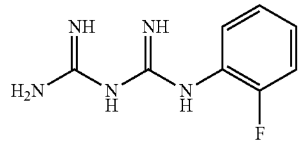 [SMILES: N=C(N)NC(=N)Nc1ccccc1F] | 1-(2-Fluorophenyl)biguanide |
| 5 | SD-000174 | 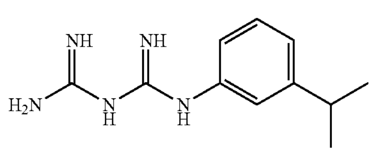 [SMILES: CC(C)c1cccc(NC(=N)NC(=N)N)c1] | 1-(3-isopropylphenyl)biguanide |

TABLE 2-continued 22 types of biguanide derivative compounds of the present invention

| No | Compound code | Compound structure | Compound name |
|---|---|---|---|
| 6 | SD-000175 | 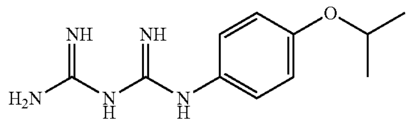 [SMILES: CC(C)Oc1ccc(NC(=N)NC(=N)N)cc1] | 1-(4-isopropoxyphenyl)biguanide |
| 7 | SD-000177 | 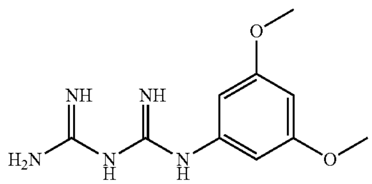 [SMILES: COc1cc(NC(=N)NC(=N)N)cc(OC)c1] | 1-(3,5-Dimethoxyphenyl)biguanide |
| 8 | SD-000178 | 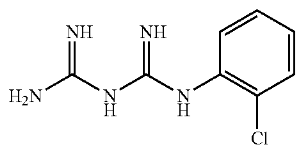 [SMILES: N=C(N)NC(=N)Nc1ccccc1Cl] | 1-(2-chlorophenyl)biguanide |
| 9 | SD-000179 | 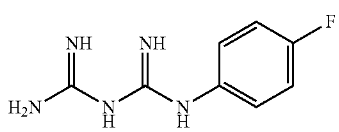 [SMILES: N=C(N)NC(=N)Nc1ccc(F)cc1] | 1-(4-fluorophenyl)biguanide |
| 10 | SD-000180 | 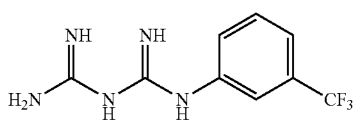 [SMILES: N=C(N)NC(=N)Nc1cccc(C(F)(F)F)c1] | 1-(3-trifluoromethylphenyl)biguanide |
| 11 | SD-000216 | 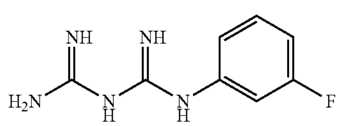 [SMILES: N=C(N)NC(=N)Nc1cccc(F)c1] | 1-(3-fluorophenyl)biguanide |
| 12 | SD-000217 | 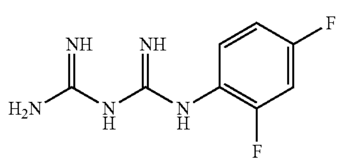 [SMILES: N=C(N)NC(=N)Nc1ccc(F)cc1F] | 1-(2,4-difluorophenyl)biguanide |
| 13 | SD-000218 | 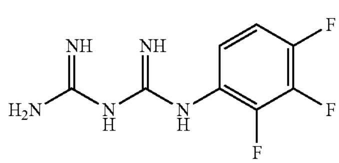 [SMILES: N=C(N)NC(=N)Nc1ccc(F)c(F)c1F] | 1-(2,3,4-trifluorophenyl)biguanide |
| 14 | SD-000219 | 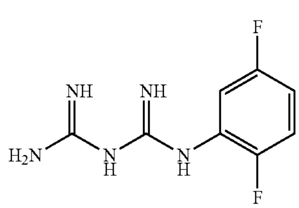 [SMILES: N=C(N)NC(=N)Nc1cc(F)ccc1F] | 1-(2,5-difluorophenyl)biguanide |
| 15 | SD-000181 | 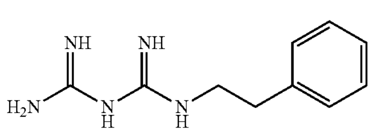 [SMILES: N=C(N)NC(=N)NCCc1ccccc1] | 1-phenethylbiguanide |

TABLE 2-continued 22 types of biguanide derivative compounds of the present invention

| No | Compound code | Compound structure | Compound name |
|---|---|---|---|
| 16 | SD-000176 | 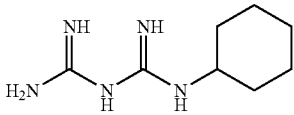 [SMILES: N=C(N)NC(=N)NC1CCCCC1] | 1-cyclohexylbiguanide |
| 17 | SD-000182 | 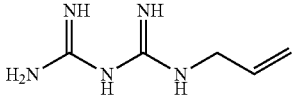 | 1-allylbiguanide |
| 18 | SD-000183 | 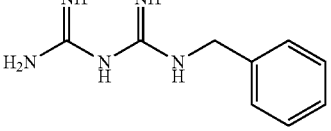 | 1-benzylbiguanide |
| 19 | SD-000184 | 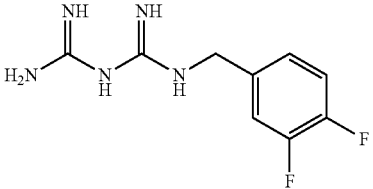 [SMILES: N=C(N)NC(=N)NCc1ccc(F)c(F)c1] | 1-(3,4-difluorobenzyl)biguanide |
| 20 | SD-000195 | 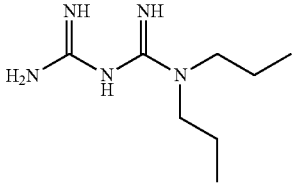 | 1,1-dipropylbiguanide |
| 21 | SD-000196 | 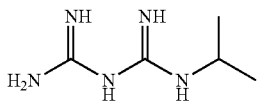 | 1-isopropylbiguanide |
| 22 | SD-000198 | 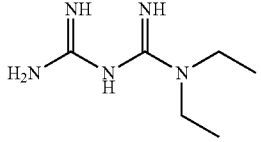 | 1,1-diethylbiguanide |

Example 2

IL-17 Inhibition Effect of Biguanide Derivative Compounds According to the Present Invention In order to verify whether the biguanide derivative compound of the present invention has the activity of increasing generation of IL-17 as an inflammatory cytokine in a Th17 cell which is a pathogenic cell, an expression degree of IL-17 was measured by an ELISA assay.

<2-1> Preparation of Cells

Spleen cells were obtained from a normal mouse of C57BL/6 (Orient Company, Korea). That is, the tissue of the spleen extracted from the mouse was finely grinded by using a teasing slide and then erythrocytes in the spleen were removed by an erythrocyte hemolysis solution. Thereafter, a PBS buffer solution was added, centrifuged, and washed to obtain spleen cells.

<2-2> Measurement of IL-17 Cytokine $1 \times 10^6$ of the spleen cells from the mouse prepared through Example <2-1> were divided in a 24-well plate coated with 0.5 g/mL of anti-CD3 antibody and simultaneously treated with 1 μg/mL of anti-CD28 antibody, 2 ng/ml of TGF-β, 20 ng/ml of IL-6 20 ng/ml, 2 μg/ml of anti-IL-4, and 2 μg/ml of anti-IFNr as a condition capable of stimulating Th17 cells, and then the cells were incubated for 3 days to induce the differentiation of the Th17 cells. In this case, the cells were treated with the biguanide derivative compound of the present invention (SD-000196: 1-isopropylbiguanide, SD-000216: 1-(3-fluorophenyl)biguanide, SD-000217: 1-(2,4-difluorophenyl)biguanide) in the concentrations of 2 μM, 20 μM, and 200 μM, respectively. A positive control group used metformin as the biguanide-based compound used as a diabetes therapeutic agent currently on the market instead of the compound of the present invention.

In order to measure an amount of the generated IL-17 cytokine, a supernatant of the incubated cells was collected and the IL-17 expression degree was examined by using a sandwich ELISA. To this end, first, 2 μg/mL of a monoclonal anti-IL-17 was reacted in a 96-well plate at 4° C. overnight and then a non-specific binding was blocked by a blocking solution (1% BSA/PBST). An IL-17 recombinant was continuously diluted by ½ concentration to be used as a standard, added with the cell-incubated supernatant, and reacted at room temperature for 2 hrs. Thereafter, biotinylated anti-IL-17 was reacted at room temperature for 2 hrs, washed four times, and then diluted and added with a diluted ExtraAvidin-alkaline phosphatase conjugate, and reacted at room temperature for 2 hrs. Thereafter, a PNPP/DEA solution was added and colored, and then the absorbance was measured at a wavelength of 405 nm.

Figure 1B:
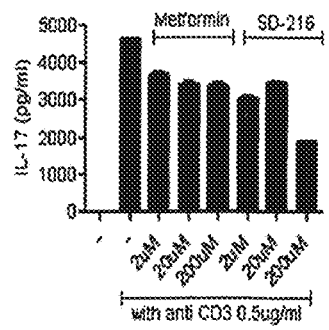
Figure 1C:
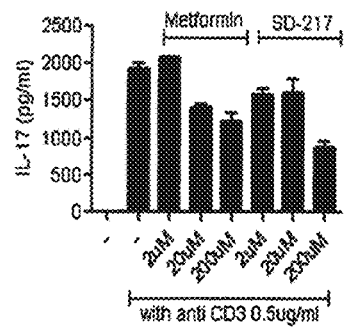

As a result, as illustrated in FIG. 1, it was verified that the generated amount of the IL-17 as the inflammatory cytokine generated from the Th17 cells as the pathogenic cells was significantly reduced when the biguanide derivative compound was treated in a concentration of 200 μM. Particularly, in the case of the SD-000196 (1-isopropylbiguanide) compound, it was shown that the IL-17 generated amount was reduced depending on the treatment concentration and it was verified that the generation of IL-17 was completely suppressed in the concentration of 200 μM (see FIG. 1A).

Example 3

TNF-α Inhibition Effect of Biguanide Derivative Compounds According to the Present Invention Since it is known that Metformin used as the diabetes therapeutic agent currently on the market has a slight effect of blocking TNF-α as the inflammatory cytokine, in order to verify whether the biguanide derivative compound of the present invention has activity of reducing the generation of TNF-α, the expression degree of TNF-α was measured by an ELISA assay.

First, 1×10$^6$ of mouse spleen cells prepared through Example <2-1> were treated with the biguanide derivative compounds of the present invention (SD-000196: 1-isopropylbiguanide, SD-000216: 1-(3-fluorophenyl)biguanide, SD-000217: 1-(2,4-difluorophenyl)biguanide) in the concentrations of 2 μM, 20 μM, and 200 μM, treated with lipopolysaccharide (LPS) in the concentration of 100 ng/ml at the same time, and cultured for 3 days in an incubator at 37° C. to induce an inflammatory response in the spleen cells. A positive control group used Metformin as the biguanide-based compound used as a diabetes therapeutic agent currently on the market instead of the compound of the present invention.

In order to measure an amount of the generated TNF-α cytokine, a supernatant of the incubated cells was collected and the TNF-α generation degree was examined by using an ELISA. 2 μg/mL of a monoclonal anti-TNF-α was reacted in a 96-well plate at 4° C. overnight and then a non-specific binding was blocked by a blocking solution (1% BSA/PBST) after the reaction. A TNF-α recombinant was continuously diluted by ½ concentration to be used as a standard, added with the cell-incubated supernatant, and reacted at room temperature for 2 hrs. Thereafter, biotinylated anti-TNF-α was reacted at room temperature for 2 hrs, washed four times, and then diluted and added with a diluted ExtraAvidin-alkaline phosphatase conjugate, and reacted at room temperature for 2 hrs. Thereafter, a PNPP/DEA solution was added and colored, and then the absorbance was measured at a wavelength of 405 nm.

Figure 2A:
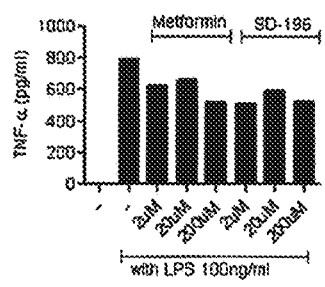
FIG. 2 is a result of analyzing an TNF-α generation amount in cells according to a concentration (2, 20, 200 μM) treatment of a biguanide derivative compound of the present invention in spleen cells isolated from mice by a sandwich ELISA method (A: SD-196, B: SD-216, C: SD-217).
Figure 2B:
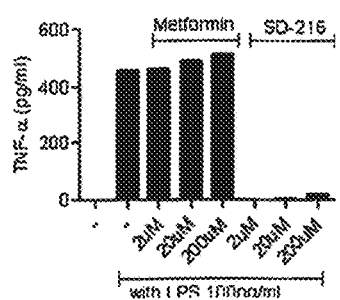
Figure 2C:
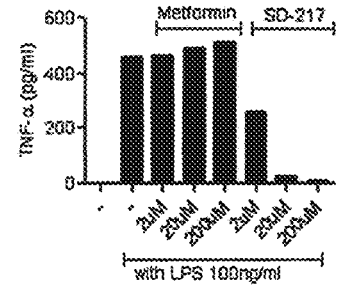
Figure 3A:
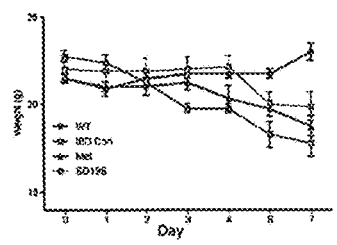
FIG. 3 is a result of observing a change in weight according to administration of the biguanide derivative compound of the present invention in an inflammatory bowel disease animal model. A to C are results of measuring a change in weight g (A: SD-196, B: SD-216, C: SD-217) and D to F are results of measuring a change in weight % (D: SD-196, E: SD-216, F: SD-217).
Figure 3B:
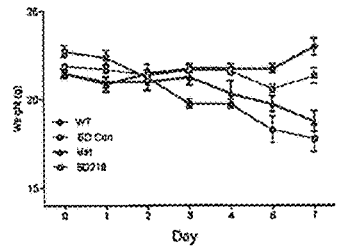
Figure 3C:
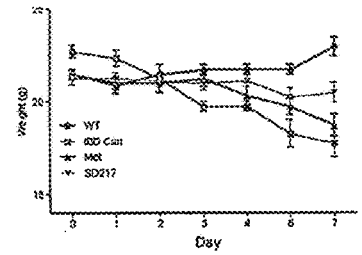
Figure 3D:
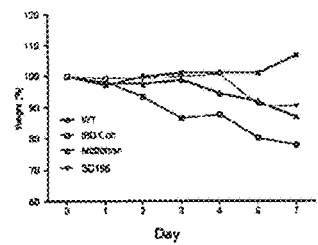
Figure 3E:
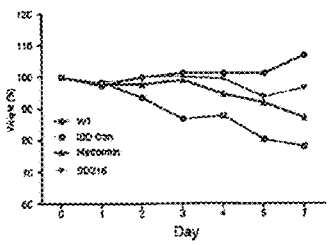
Figure 3F:
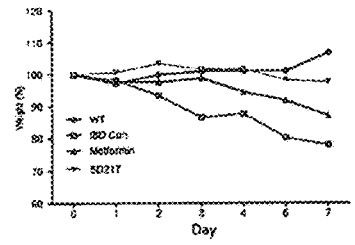

As a result, as illustrated in FIG. 2, it was verified that the generated amount of TNF-α was reduced in an experimental group treated with the biguanide derivative compounds of the present invention as compared with a case treated with only LPS. Particularly, it was shown that in the experimental groups treated with SD-000216 (1-(3-fluorophenyl)biguanide) and SD-000217 (1-(2,4-difluorophenyl)biguanide) compounds, the generated amounts of TNF-α were very significantly reduced.

Example 4

Analysis of Inflammatory Bowel Disease Therapeutic Effect of Biguanide Derivative Compounds of the Present Invention <4-1> Measurement of Change in Weight after Applying Compound of the Present Invention in Inflammatory Bowel Disease Animal Model As listed in Table 3 below, an experimental animal (C57BL/6, 6-week-old) was divided into four experimental groups and added with 3.5% dextran sodiumsulfate (DSS) for 4 days to cause inflammation, and then the biguanide derivative compounds (SD-000196: 1-isopropylbiguanide, SD-000216: 1-(3-fluorophenyl)biguanide, SD-000217: 1-(2,4-difluorophenyl)biguanide) of the present invention were orally administrated by 1 mg and administrated in the rectal by 2 mg at the same time. While a progression degree of the inflammatory bowel disease over time was observed every day in the mouse, a change in weight was measured every day and further, the weight was converted to % and the degree of the effect of treating/improving the disease was evaluated. A positive control group used metformin (Sigma Aldrich, animal experiment dose: 1 mg of oral dose, 2 mg of rectal dose) as the biguanide-based compound used as a diabetes therapeutic agent currently in the market instead of the compound of the present invention.

For reference, the DSS is administrated by drinking water and corresponds to a chemical which kills the colon epithelial cells and causes colonic inflammation, and a DSS colitis model corresponds to an established model of an experimental inflammatory bowel disease (IBD).

TABLE 3

| Four experimental groups | | | |
| --- | --- | --- | --- |
| Experimental group | Experimental material | Dose | Number of mice |
| WT (wild type) | Non-treated | — | 10 |
| IBM control group | 3.5% DSS | 3 mg | 10 |
| Metformin-treated group | 3.5% DSS + Metformin | 3 mg | 10 |
| Biguanide derivative compound-treated group | 3.5% DSS + (SD-000196) | 3 mg | 10 |
| | 3.5% DSS + (SD-000216) | 3 mg | 10 |
| | 3.5% DSS + (SD-000217) | 3 mg | 10 |

As a result, as illustrated in FIG. 3, it was verified that in the case of an experimental group administrated with the biguanide derivative compound of the present invention, as compared with an inflammatory bowel disease-induced animal model (IBM control group), the weight was significantly improved and become similar to the weight of a normal mouse (WT) over time.

<4-2> Measurement of Degree of Tissue Inflammation after Applying Compound of the Present Invention in Inflammatory Bowel Disease Animal Model In the case of administrating the biguanide derivative compound of the present invention in the inflammatory bowel disease animal model of Example <4-1>, a cell inflammation degree in the colon tissue of the mouse was examined by an immunohistochemical staining method.

The immunohistochemical staining method was performed by the following process. The colon tissue of the mouse experimental group in Table 1 was isolated, fixed with 10% neutral buffered formalin, and embedded with paraffin, and then a joint tissue was made into a slice in a thickness of 7 µm and attached to a slide. The colon tissue passed through a deparaffinization process by using xylene before proceeding basic straining and then hydrated with ethanol from a high concentration to a low concentration. The straining process performed hematoxylin/eosin straining and analyzed by an optical microscope.

Figure 4:
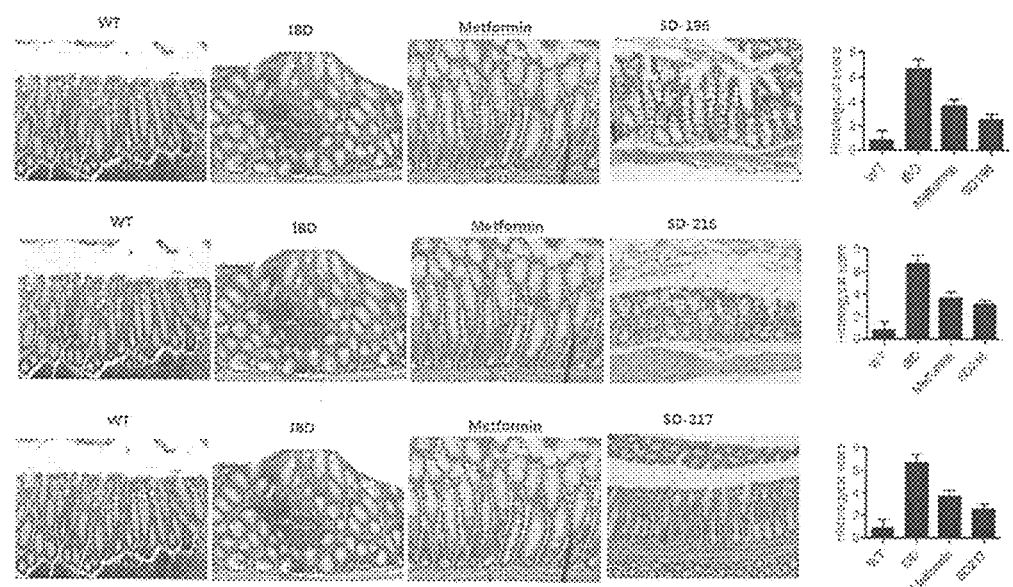
FIG. 4 is a result of observing a degree of tissue damage by inflammation in a colon tissue according to administration of the biguanide derivative compound of the present invention in an inflammatory bowel disease animal model by an immunohistochemical staining method.

As a result, as illustrated in FIG. 4, in the colon tissue of the inflammatory bowel disease mouse experimental group fed with the DSS, it was observed that a loss was large and the cells were penetrated, whereas in the colon tissue of the experimental group administrated with the biguanide derivative compound of the present invention to the inflammatory bowel disease mouse, it was verified that the damage was small and the penetration of the cells was low.

<4-3> Measurement of TNF-α Expression after Applying Compound of the Present Invention in Inflammatory Bowel Disease Animal Model In the case of treating the biguanide derivative compound of the present invention in the inflammatory bowel disease animal model of Example <4-1>, a degree of intracellular TNF-α expression in the colon tissue of the mouse was examined by an immunohistochemical staining method.

The immunohistochemical staining method was performed similarly to Example <4-2> and a TNF-α antibody was reacted and colored with DAB, and then analyzed by an optical microscope.

Figure 5:
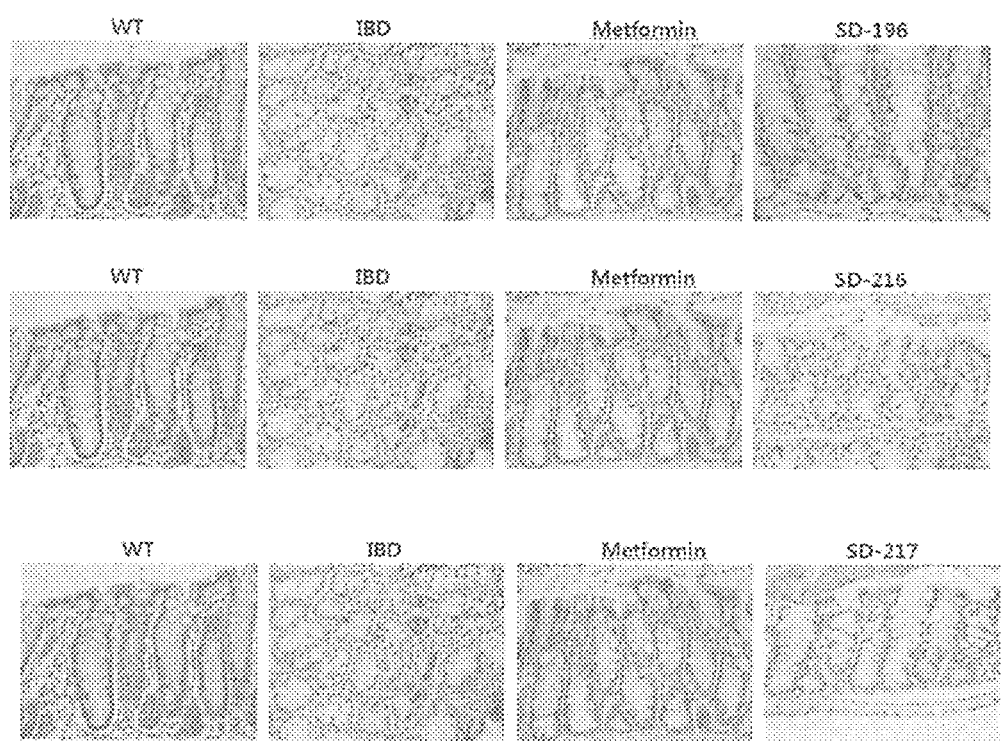
FIG. 5 is a result of observing a degree of intracellular TNF-α expression in a colon tissue according to administration of the biguanide derivative compound of the present invention in an inflammatory bowel disease animal model by an immunohistochemical staining method.

As a result, as illustrated in FIG. 5, in an inflammatory bowel disease mouse experimental group fed with the DSS, it was observed that the TNF-α as the intracellular inflammatory cytokine was very increased, whereas in an experimental group administrated with the biguanide derivative compound of the present invention to the inflammatory bowel disease mouse, it was verified that the intracellular expression of TNF-α was reduced. Further, it was observed that the TNF-α expression degree was very low as compared with a metformin treated group as a positive control group.

Example 5

Alloresponse Suppression Effect of Biguanide Derivative Compounds According to the Present Invention In the experiment, in order to examine whether the biguanide derivative compounds have an effect of suppressing an alloresponse, in vitro, $2\times10^5$ of CD4+T cells of a normal responder (Balb/c) per well and $2\times10^5$ of T cell removal spleen cells derived from a responder (isomorphous) or a stimulator (C57BL/6, dimorphous) irradiated by radiation were added in a 96-well round bottom plate, mixed, and incubated to induce an alloresponse. Further, the biguanide derivative compounds (SD-000196:1-isopropyl-biguanide, SD-000216: 1-(3-fluorophenyl)biguanide, SD-000217: 1-(2,4-difluorophenyl)biguanide) of the present invention or metformin were treated together and incubated for 4 days, and then in the T cell proliferation reaction degree in the incubated cells, an effect on an alloresponse of the biguanide derivative compounds of the present invention was analyzed by using a 3H incorporation method.

Figure 6A:
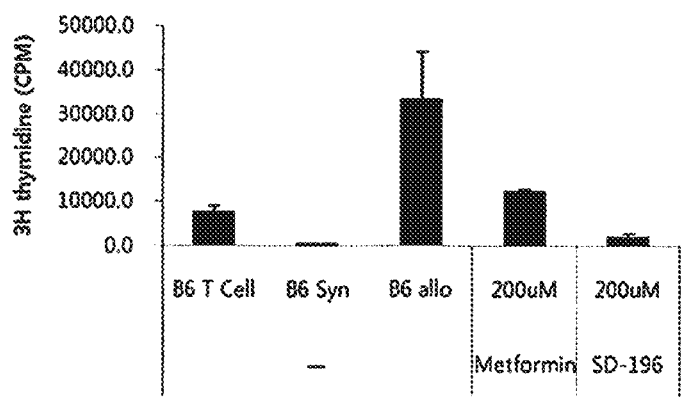
FIG. 6 illustrates a result of analyzing an alloresponse inhibition degree of the derivative compound by treating the biguanide derivative compound of the present invention in spleen cells with the induced alloresponse and measuring a T cell proliferation degree (A: SD-196 compound treatment result, B: SD-216 compound treatment result, C: SD-217 compound treatment result).
Figure 6B:
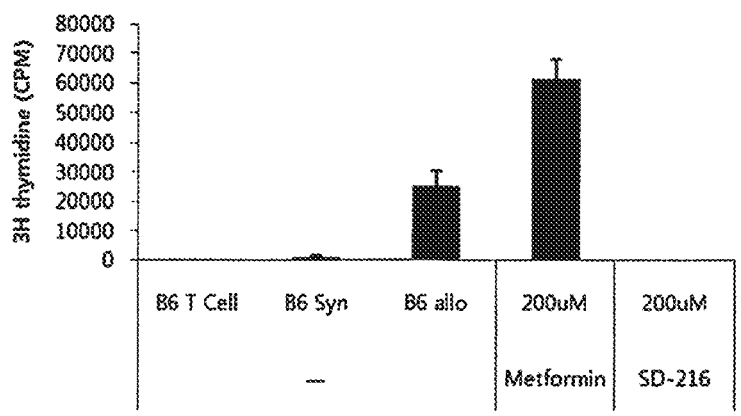
Figure 6C:
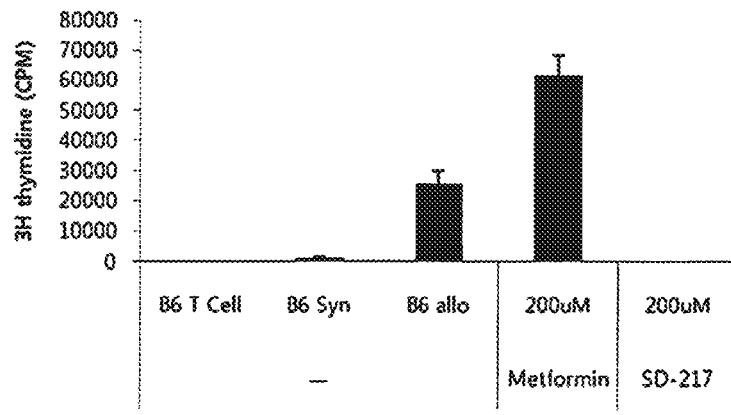

As a result, as illustrated in FIG. 6, it was verified that in an experimental group treated with the biguanide derivative compound of the present invention, the alloresponse was significantly suppressed and an immune response was more effectively suppressed as compared with the group treated with metformin.

Accordingly, through the result, the inventors found a fact that the biguanide derivative compounds of the present invention effectively suppressed the alloresponse generated in the transplantation process and successfully induced an allograft.

Example 6

Effect of Increasing Regulatory T Cell Activity of Biguanide Derivative Compounds According to the Present Invention In the experiment, whether the activity of regulatory T cells (hereinafter, briefly abbreviated as 'Treg') of the biguanide derivative compound was increased was examined.

The Treg cells have characteristics of suppressing the function of the abnormally activated immune cells and controlling the inflammatory response and many experiments proving that the immune diseases and the inflammatory diseases are effectively treated by an action of increasing the activity of the Treg cells have been reported. Accordingly, the experiment was performed in order to prove that the biguanide derivative compounds of the present invention can be used as an immune therapeutic agent by the action of increasing the activity of the Treg cells.

The activity of Treg cells was examined by using a flow cytometry method. Specifically, In vitro, $2\times10^5$ of CD4+T cells of a normal responder (Balb/c) per 96-well and $2\times10^5$ of T cell removal spleen cells derived from a responder (isomorphous) or a stimulator (C57BL/6, dimorphous) irradiated by radiation were added, mixed, and incubated to induce an alloresponse. In this case, in the alloresponse, the biguanide derivative compounds (SD-000196: 1-isopropyl-biguanide, SD-000216: 1-(3-fluorophenyl)biguanide, SD-000217: 1-(2,4-difluorophenyl)biguanide) of the present invention or metformin were treated together and incubated for 4 days, and then the differentiated regulatory T cells were analyzed by a flow cytometer by using anti-CD4-percp, anti-CD25-APC, and anti Foxp3-Pe fluorescent antibodies.

Figure 7A:
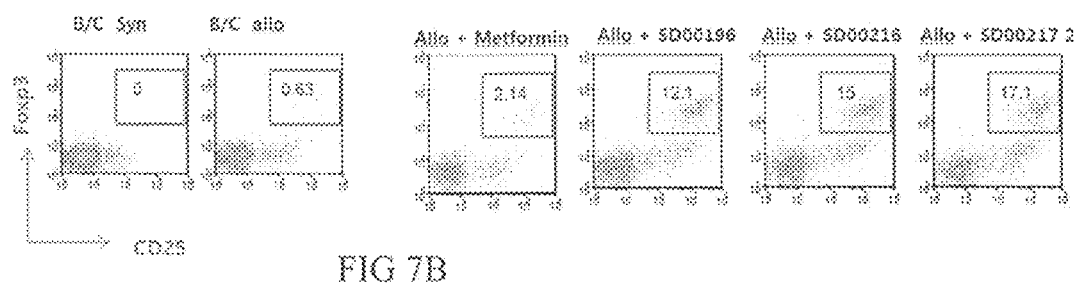
FIG. 7 illustrates (A) a graph of verifying the expression degree of Treg cells (Foxp3+CD25+ Treg cells) by an FACS analysis by treating a biguanide derivative compound of the present invention in spleen cells with the induced alloresponse and (B) a result of quantifying the number of Treg cells (Foxp3+CD25+Treg cells) by a graph.
Figure 7B:
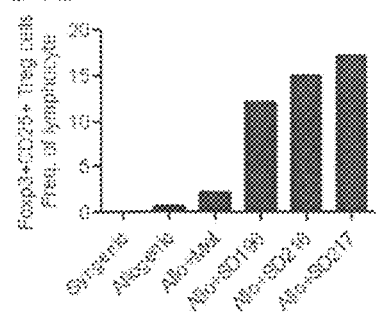

As a result, as illustrated in FIG. 7, it was verified that in an experimental group treated with the biguanide derivative compound of the present invention, the activity and the number of Treg cells were significantly increased and the activity of Treg cells was more significantly increased as compared with the group treated with only metformin.

Through the above result, the biguanide derivative compound of the present invention may suppress the alloresponse and simultaneously increase the Treg activity to have an ideal immunomodulatory function.

Example 7

Analysis of Acute Graft Versus Host Disease (aGVHD) Therapeutic Effect of Biguanide Derivative Compound of the Present Invention Through Examples 5 and 6, it was verified that the biguanide derivative compound of the present invention had an effect of suppressing the alloresponse and simultaneously increasing the Treg activity, and in the experiment, whether the biguanide derivative compounds of the present invention improve and treat symptoms of the aGVHD was examined.

To this end, an aGVHD model was prepared, and a responder mouse Balb/c (H-2 k/d) was totally body-irradiated (TBI) by 800 cGy and hematopoietic stem cells and spleen cells were isolated from the femur and tibia of a donor mouse C57BL/6 (H-2 k/b) and $5 \times 10^6$ of the hematopoietic stem cells and $8 \times 10^6$ of the spleen cells were transplanted to the responder mouse Balb/c (H-2 k/d). Metformin or the biguanide derivative compounds (SD-000196: 1-isopropylbiguanide, SD-000216: 1-(3-fluorophenyl)biguanide, SD-000217: 1-(2,4-difluorophenyl)biguanide) of the present invention was treated in the spleen cells before transplantation in the concentration of 5 mM for 2 hrs and then the survival degree of the aGVHD-induced mice was evaluated.

Figure 8A:
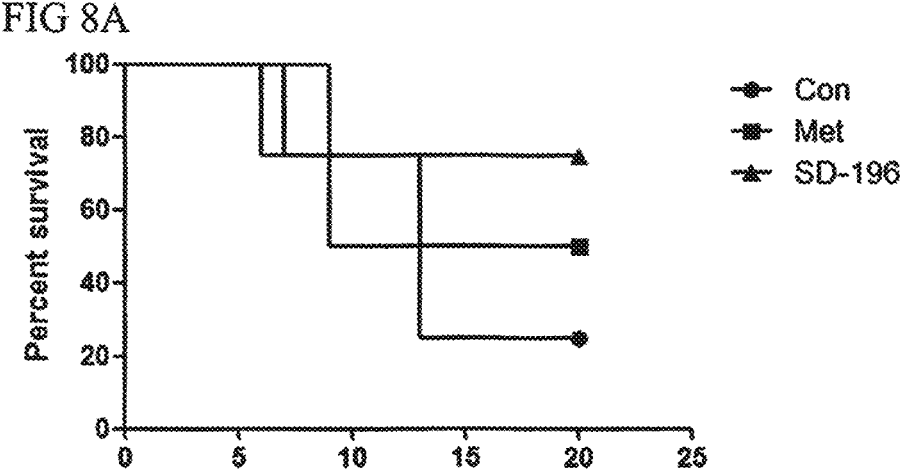
FIG. 8 is a graph of measuring a survival rate of animals over time after administrating a biguanide derivative compound of the present invention in an acute graft versus host disease animal model.
Figure 8B:
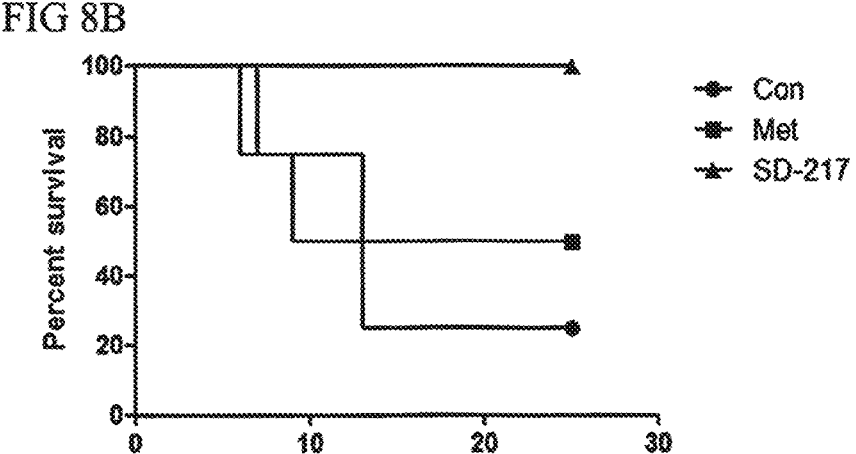
Figure 9A:
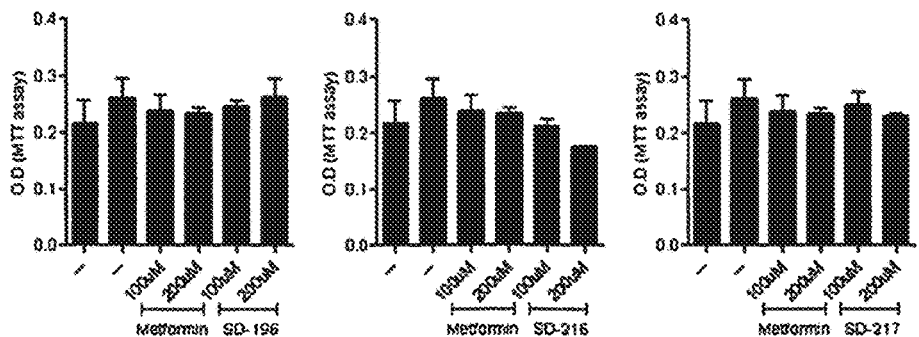
FIG. 9 is a result of measuring cytotoxicity (MTT assay) (A), IgG generation (B), and IL-17 and TNF-α inflammatory cytokines (C) in a rheumatoid arthritis animal model in order to evaluate an arthritis therapeutic effect of the biguanide derivative compound of the present invention.
Figure 9B:
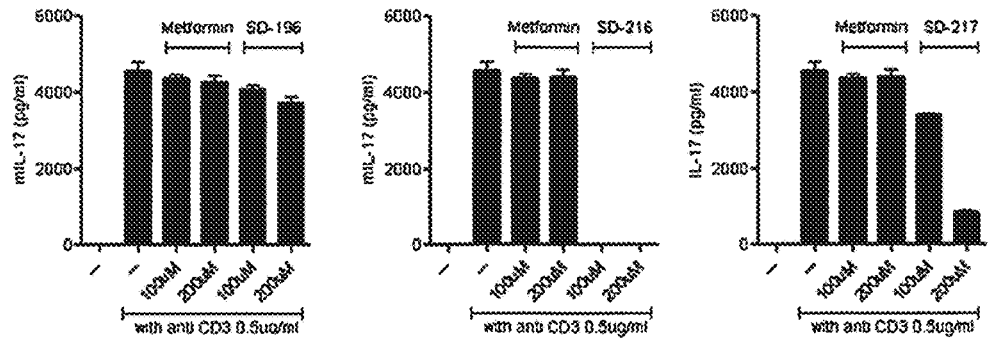
Figure 9C:
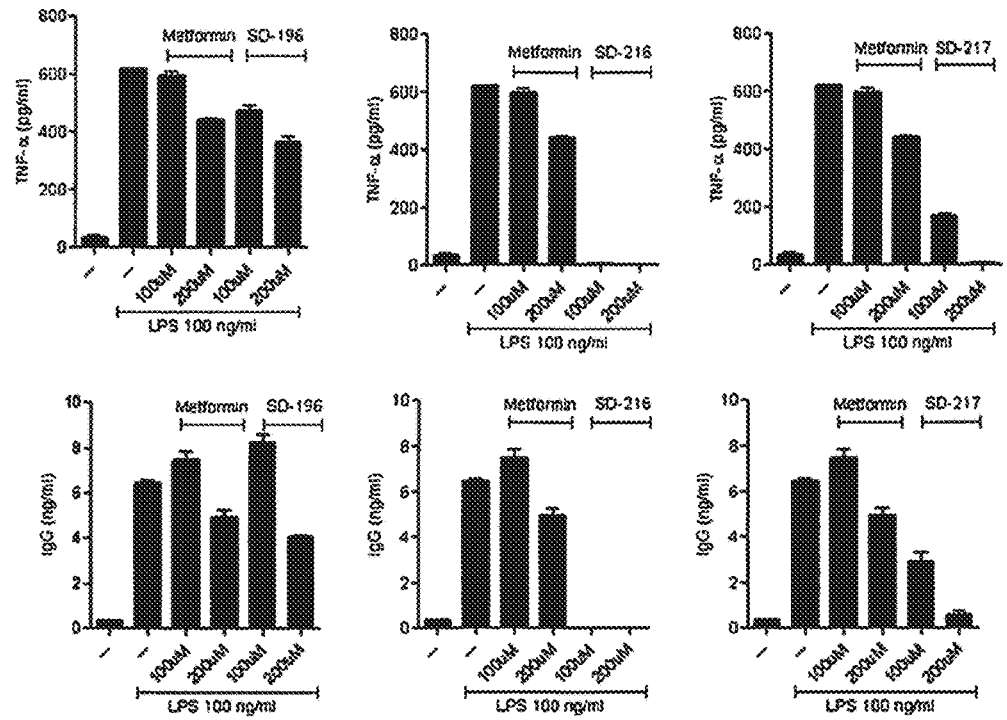

As a result, as illustrated in FIG. 8, it was verified that in an experimental group treated with the biguanide derivative compound of the present invention, the survival of the mice was significantly increased as compared with an aGVHD mouse group and an aGVHD mouse group treated with metformin.

Example 8

Arthritis Therapeutic Effect of Biguanide Derivative Compound of the Present Invention In order to evaluate an arthritis therapeutic effect of the biguanide derivative compound of the present invention, in a rheumatoid arthritis animal model, cytotoxicity, generation of autoantibody, expression of inflammatory cytokines and regulatory T cells (Treg), and osteoclast differentiation were measured. Like Examples, metformin was used as a control group.

<8-1> MTT Assay

In order to examine cytotoxicity of the biguanide derivative compound of the present invention, an MTT assay was performed. Cells were isolated from the spleen in a normal mouse group and the isolated cells were incubated for 3 days in the concentration of 0.5 μg/ml of anti-CD3 or 100 ng/ml of LPS 100, and metformin, SD-196, SD-216 or SD-217 was treated for each concentration and incubated for 3 days. The MTT was treated before 4 hrs of harvest and the cytotoxicity was evaluated, and as a result, it was verified that there was no cytotoxicity of SD-196, 216 and 217 (see FIG. 9A).

<8-2> IgG Measurement

In order to examine an effect of suppressing the generation of autoantibody of the biguanide derivative compound of the present invention, the incubated supernatant was collected and the IgG expression degree was examined by using an ELISA. A monoclonal anti-IgG was reacted at 4° C. overnight in a 96-well plate and then a non-specific binding was blocked by a blocking solution. A mouse control serum was continuously diluted by ½ to be used as a standard, added with the cell-incubated supernatant, and reacted at room temperature for 2 hrs. Thereafter, HRP-anti-IgG was reacted at room temperature for 2 hrs, washed four times after reaction, added with the diluted HRP-conjugate, and reacted at room temperature for 2 hrs. The HRP-anti-IgG was colored and the absorbance was measured at a wavelength of 405 nm, and as a result, it was verified that SD-196, 216 and 217 significantly suppressed the expression of IgG as compared with metformin.

<8-3> Measurement of Inflammatory Cytokines and Examination of Regulatory T Cell (Treg) Activity In order to evaluate an effect of suppressing the expression of the inflammatory cytokine of the biguanide derivative compound of the present invention, the incubated supernatant was collected and the expression degrees of IL-17 and TNF-α of a mouse were examined by using a sandwich ELISA. 2 g/mL of a monoclonal anti-IL-17 or anti-TNF-α was reacted in a 96-well plate at 4° C. overnight and then a non-specific binding was blocked by a blocking solution (1% BSA/PBST) after the reaction. An IL-17 or TNF-α recombinant was continuously diluted by ½ to be used as a standard, added with the cell-incubated supernatant, and reacted at room temperature for 2 hrs. Thereafter, biotinylated anti-IL-17 or anti-TNF-α was added and reacted at room temperature for 2 hrs, washed four times after the reaction, diluted with a diluted ExtraAvidin-alkaline phosphatase conjugate, and reacted at room temperature for 2 hrs. After the reaction, a PNPP/DEA was added and colored, and absorbance was measured at a wavelength of 405 nm. As a result, it was verified that the IL-17 and TNF-α inflammatory cytokines were significantly suppressed by SD-196, 216 and 217 (see FIG. 9C).

Figure 10:
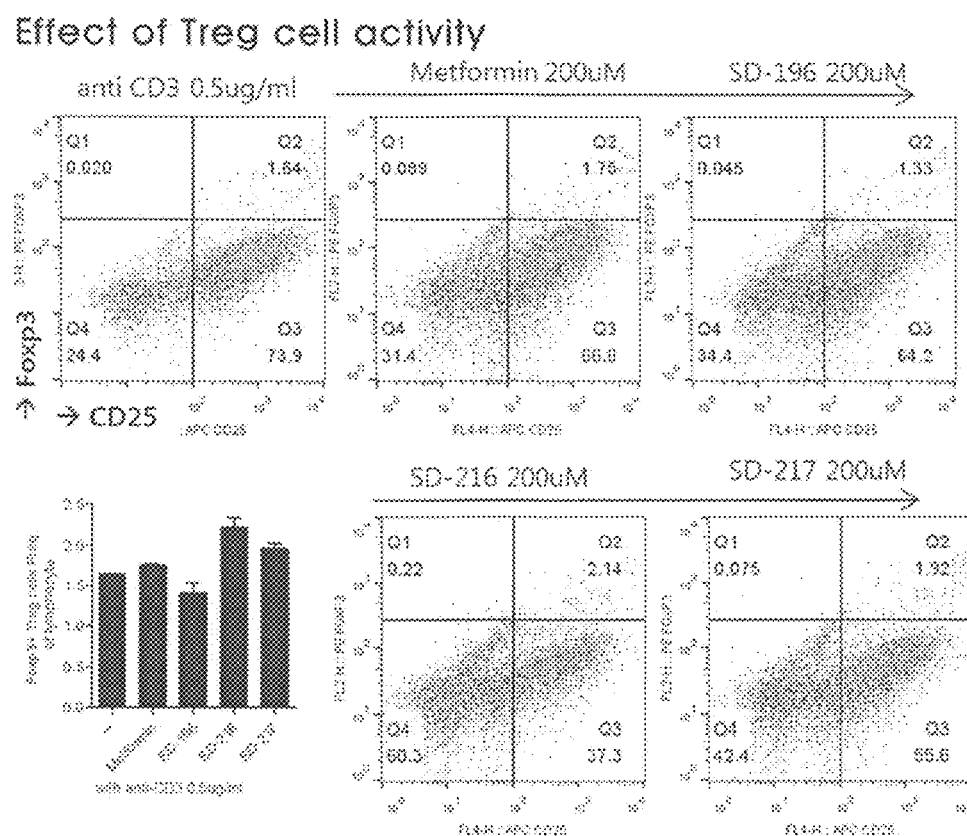
FIG. 10 is a result of measuring expression of regulatory T cell (Treg) in a rheumatoid arthritis animal model in order to evaluate an arthritis therapeutic effect of the biguanide derivative compound of the present invention.
Figure 11:
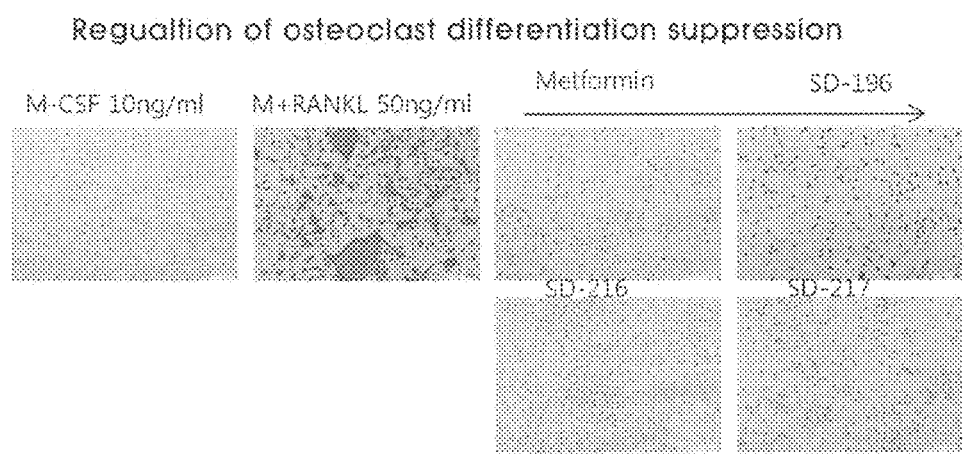
FIG. 11 is a result of measuring osteoclast differentiation (TRAP staining) in a rheumatoid arthritis animal model in order to evaluate an arthritis therapeutic effect of the biguanide derivative compound of the present invention.

Further, in order to examine whether the biguanide derivative compound of the present invention activates the expression of regulatory T cells (Treg), the incubated cells were flow-cytometry by using anti-CD4-percp, anti-CD25-APC, and anti Foxp3-Pe fluorescent antibodies (ab), and as a result, it was verified that SD-196, 216 and 217 activated the Foxp3+Treg cells (see FIG. 10).

<8-4> Examination of Osteoclast Differentiation Regulation

In order to verify whether the biguanide derivative compound of the present invention suppresses the osteoclast differentiation, while a bone marrow extracted from a leg in an arthritis animal model was treated with MCSF (10 ng/ml) and RANKL (50 ng/ml) to differentiate the osteoclast, metformin, SD-196, SD-216, and SD-217 were treated, respectively, and the differentiation degrees of the osteoclast were evaluated. The evaluation was performed by using TRAP straining. As a result, it is verified that SD-196, 216 and 217 significantly suppress the differentiation of the osteoclast (see FIG. 11).

Figure 12A:
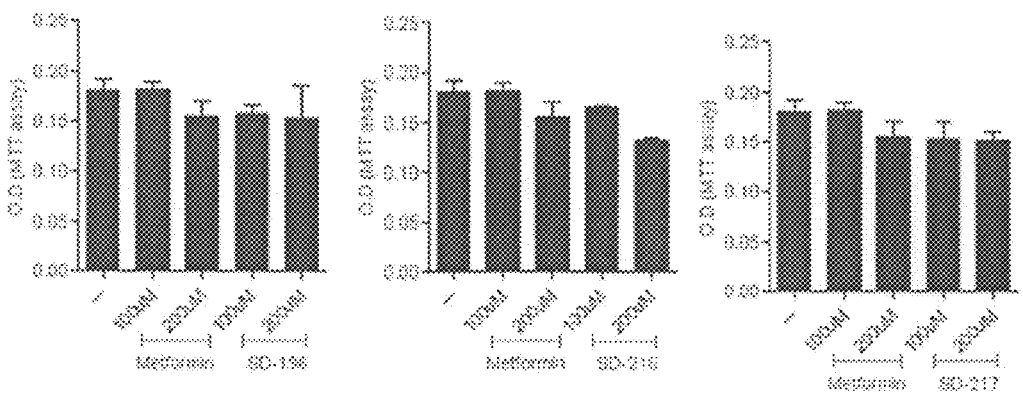
FIG. 12 is a result of measuring cytotoxicity (MTT assay) (A) and expression of IL-17 inflammatory cytokine (B) in an animal model in order to evaluate a therapeutic effect of rheumatoid arthritis with metabolic syndrome of the biguanide derivative compound of the present invention.
Figure 12B:
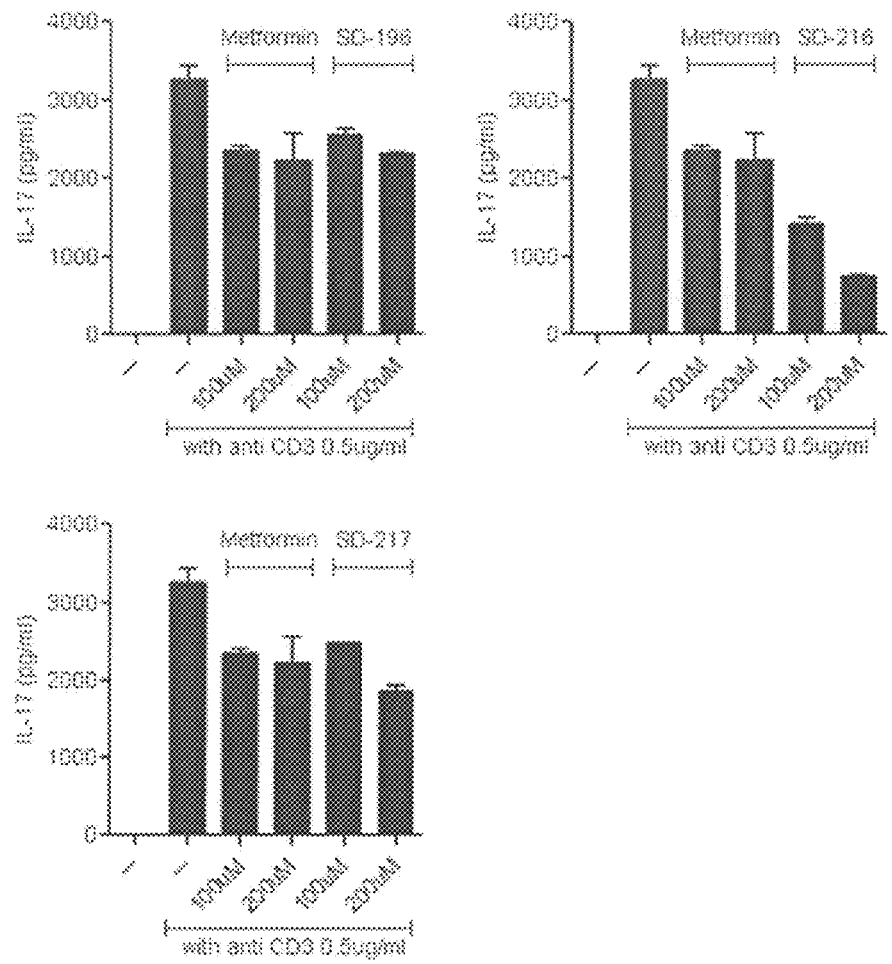
Figure 13:
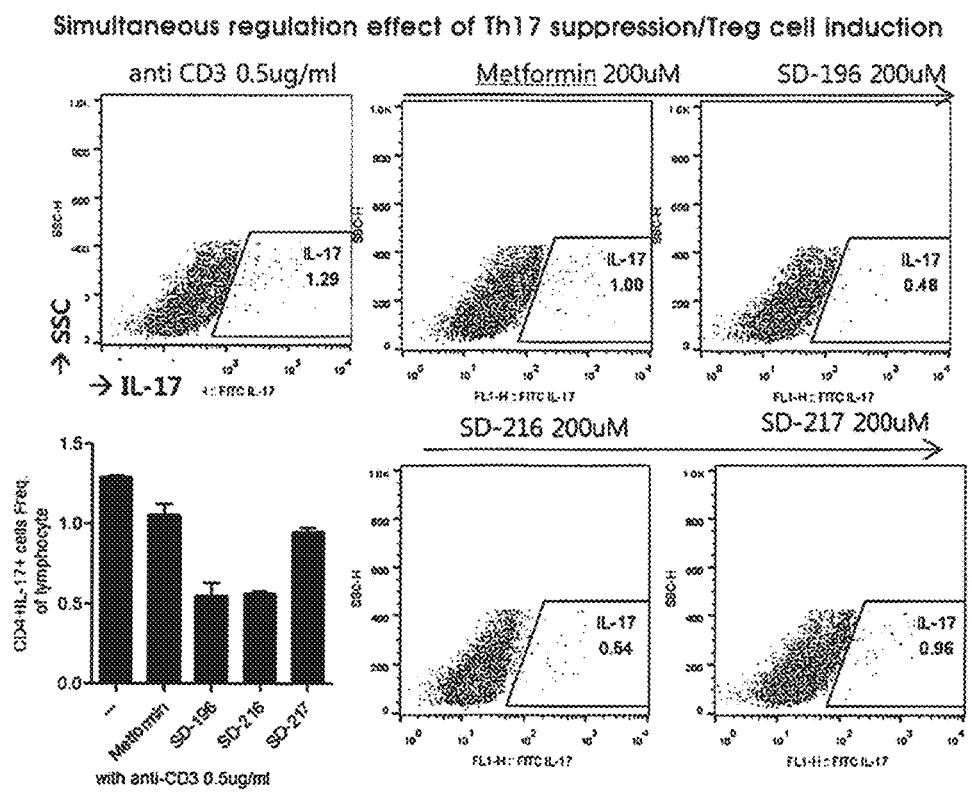
FIG. 13 is a result of measuring expressions of Th17 and regulatory T cell (Treg) in an animal model in order to evaluate a therapeutic effect of rheumatoid arthritis with metabolic syndrome of the biguanide derivative compound of the present invention.

<8-5> Evaluation of Therapeutic Effect in Rheumatoid Arthritis Disease Model with Metabolic Syndrome As the result of measuring the expressions of cytotoxicity and inflammatory cytokines in a rheumatoid arthritis disease model with a metabolic syndrome by the same method as Examples <8-1> and <8-3>, SD-196, 216 and 217 did not have the cytotoxicity (see FIG. 12A) and suppressed the expression of IL-17 (see FIG. 12B). Further, the incubated cells were analyzed by flow cytometry using anti-CD4-percp and anti-IL-17-Pe fluorescent antibodies, and as a result, it was verified that SD-196, 216 and 217 suppressed the activity of Th17 and simultaneously activated the expression of the regulatory T cells (Treg) (see FIG. 13).

Example 9

Lupus Therapeutic Effect of Biguanide Derivative Compound of the Present Invention In order to evaluate a lupus therapeutic effect of the biguanide derivative compound of the present invention, in a lupus animal model, cytotoxicity, autoantibody generation, generation of inflammatory cytokines, and Th17 regulation were measured by the same method as Example 8.

Figure 14A:
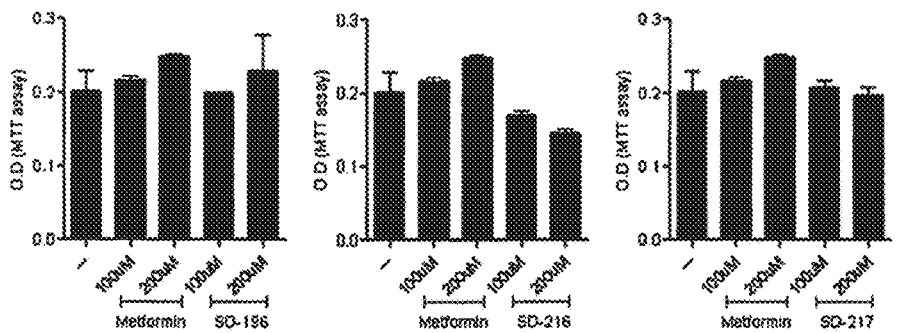
FIG. 14 is a result of measuring cytotoxicity (MTT assay) (A), IgG generation (B), and a change in expression of IL-17 and TNF-α inflammatory cytokines (C) in a lupus animal model in order to evaluate a lupus therapeutic effect of the biguanide derivative compound of the present invention.
Figure 14B:
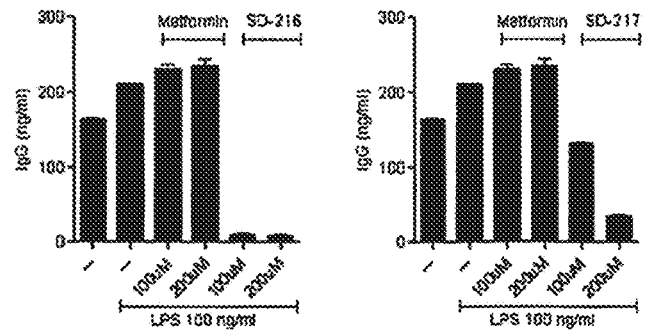
Figure 14C:
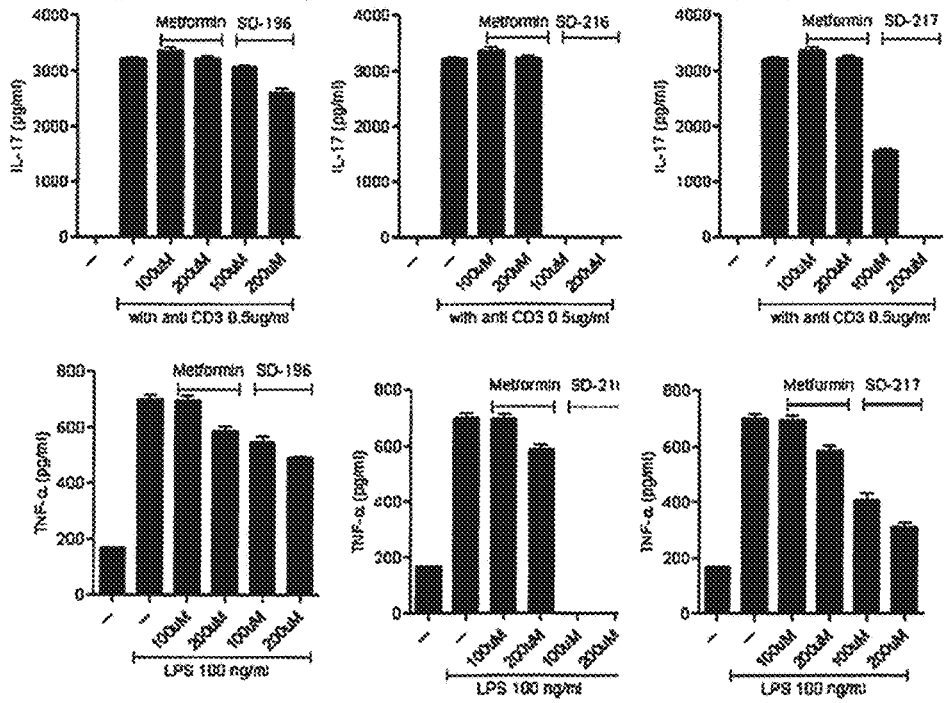
Figure 15:
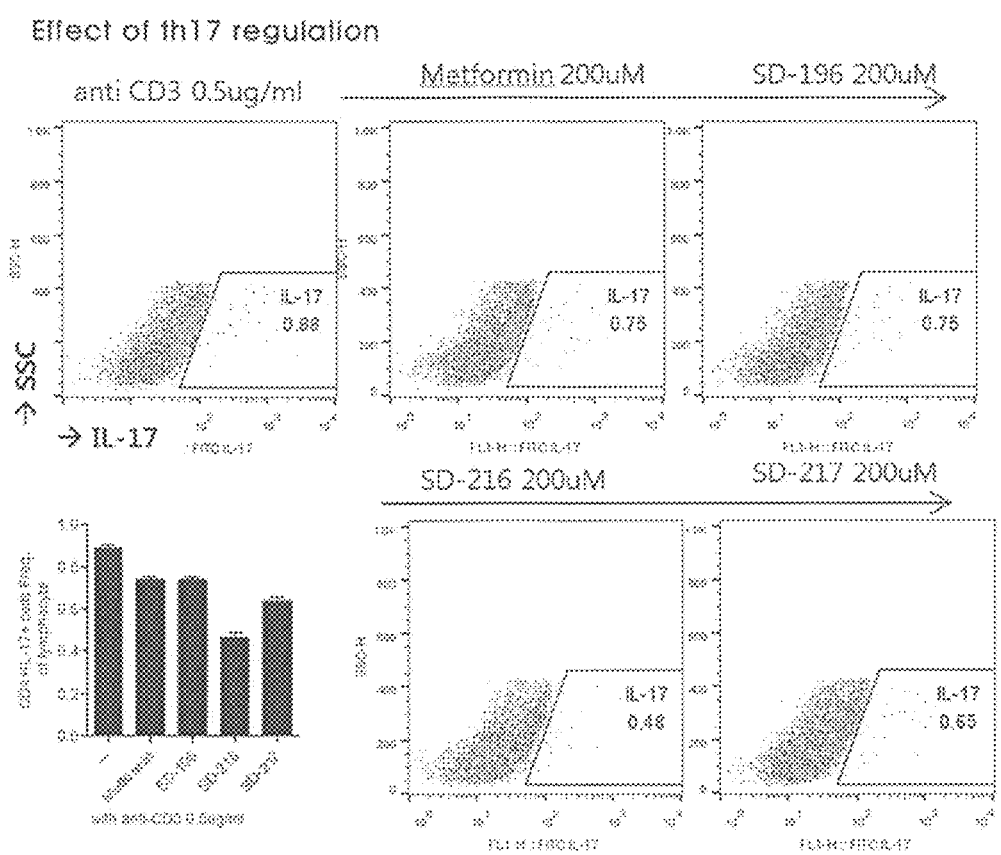
FIG. 15 is a result of measuring a change in Th17 activity in a lupus animal model in order to evaluate a lupus therapeutic effect of the biguanide derivative compound of the present invention.

As a result, it was verified that there was no cytotoxicity of SD-196, 216 and 217 (see FIG. 14A), and it was verified that SD-196, 216 and 217 significantly suppressed the expression of IgG as compared with metformin (see FIG. 14B), and suppressed the expressions of IL-17 and TNF-α inflammatory cytokines and the activity of Th17 (see FIGS. 14C and 15).

Example 10

Evaluation of Activity of Biguanide Derivative Compound of the Present Invention to Human Cells In order to evaluate a development possibility of the biguanide derivative compound of the present invention as an agent for preventing or treating immune diseases, effects of modulating cytotoxicity and generation of inflammatory cytokines by targeting normal cells were measured by the same method as Example 8.

As a result, it was verified that there was no cytotoxicity of SD-216 and 217 (see FIG. 16A) and the SD-216 and 217 suppressed the expression of TNF-α as the inflammatory cytokine as compared with metformin (see FIG. 16B).

For now, the present invention has been described with reference to the exemplary embodiments. It is understood to those skilled in the art that the present invention may be implemented as a modified form without departing from an essential characteristic of the present invention. Therefore, the disclosed exemplary embodiments should be considered from not a limitative viewpoint but an explanatory viewpoint. The scope of the present invention is described in not the above description but the appended claims, and it should be analyzed that all differences within the scope equivalent thereto are included in the present invention.

The invention claimed is:

1. A method for treating an inflammatory bowel disease or a graft versus host disease in a subject, comprising administering a pharmaceutical composition comprising a biguanide derivative or a pharmaceutically acceptable salt thereof as an active ingredient,
    wherein the biguanide derivative is 1-isopropylbiguanide or 1-(3-fluorophenyl)biguanide.

2. The method of claim 1, wherein the biguanide derivative is characterized by reducing or suppressing the generation of an inflammatory cytokine.

3. The method of claim 2, wherein the inflammatory cytokine is IL-17 or TNF-α.

4. The method of claim 1, wherein the biguanide derivative is characterized by promoting or increasing the activity of a regulatory T cell.

5. The method of claim 1, wherein the biguanide derivative is included in the composition at the concentration of 1 μM to 1,000 μM.

6. The method of claim 1, wherein the composition is administered to the subject in an amount of 1 to 100 mg per 1 kg body weight of the subject.

* * * * *